(12) United States Patent
Classen

(10) Patent No.: US 6,584,472 B2
(45) Date of Patent: *Jun. 24, 2003

(54) METHOD, SYSTEM AND ARTICLE FOR CREATING AND MANAGING PROPRIETARY PRODUCT DATA

(75) Inventor: John Barthelow Classen, Baltimore, MD (US)

(73) Assignee: Classen Immunotherapies, Inc., Baltimore, MD (US)

(*) Notice: Subject to any disclaimer, the term of this patent is extended or adjusted under 35 U.S.C. 154(b) by 298 days.

This patent is subject to a terminal disclaimer.

(21) Appl. No.: 09/804,289

(22) Filed: Mar. 12, 2001

(65) Prior Publication Data

US 2001/0020240 A1 Sep. 6, 2001

Related U.S. Application Data

(63) Continuation-in-part of application No. 09/449,178, filed on Nov. 24, 1999, now Pat. No. 6,219,674.

(51) Int. Cl.[7] .............................................. G06F 17/00
(52) U.S. Cl. ........................ 707/104.1; 705/3; 600/300
(58) Field of Search .............................. 707/100, 104.1; 705/3; 600/300; 395/203

(56) References Cited

U.S. PATENT DOCUMENTS

| 5,642,731 A | 7/1997 | Kehr ........................... 128/630 |
| 5,737,539 A | 4/1998 | Edelson et al. .............. 395/203 |
| 5,833,599 A | 11/1998 | Schrier et al. ............... 600/300 |
| 5,845,255 A | 12/1998 | Mayaud .......................... 705/3 |
| 5,876,926 A | 3/1999 | Beecham ......................... 435/5 |
| 5,908,383 A | 6/1999 | Brynjestad ................... 600/300 |
| 5,970,463 A | 10/1999 | Cave et al. ...................... 705/3 |
| 6,000,828 A | 12/1999 | Leet ............................ 364/401 |
| 6,112,182 A * | 8/2000 | Akers et al. ..................... 705/2 |
| 2002/0138305 A1 * | 9/2002 | Watanabe et al. ............... 705/2 |

OTHER PUBLICATIONS

Chen et al., "Vaccine Safety Datalink Project: A New Tool for Improving Vaccine Safety Monitoring in the United States", *Pediatrics*, vol. 99, No. 6 (Jun. 1997).

DeStefano et al., "Timing of Hepatitis B Vaccination and Risk of Insulin–Dependent Diabetes Mellites", *Pharmacoepidemiology and Drug Safety*, vol. 6, Supplement 2 (1997).

Bradbury, D. A bitter pill to swallow. Computing. Feb. 9, 1995, pp. 34–35.

* cited by examiner

*Primary Examiner*—Diane D. Mizrahi
*Assistant Examiner*—Michael Spiegel
(74) *Attorney, Agent, or Firm*—Evelyn H. McConathy; Dilworth Paxson LLP

(57) ABSTRACT

The mechanism comprises systems, methods and computerized data management device for creating and using data relating to a medical or non-medical product or device to enhance the safety of the product or device. Vast amounts of data is received regarding adverse events associated with a particular product or device, which data is analyzed in light of known adverse events associated with the product or device. At least one proprietary database of newly discovered adverse event information is created and utilized, and new characteristics of or uses for the product or device are determined. Adverse event information is gathered for a large number of population sub-groups. The system may also be programmed to incorporate the information into intellectual property and contract documents. Manufacturers and/or distributors can include the proprietary information in consumer safety information, which accompanies the product or device, or which is provided to patients, users, consumers and the like, or in the case of certain medical products or devices, to prescribers of those products or devices.

137 Claims, 6 Drawing Sheets

METHOD, SYSTEM AND ARTICLE FOR CREATING AND MANAGING PROPRIETARY PRODUCT DATA

REFERENCE TO RELATED APPLICATIONS

This application is a continuation-in-part of U.S. Ser. No. 09/449,178, filed Nov. 24, 1999 now U.S. Pat. No. 6,219,674.

FIELD OF THE INVENTION

The present invention relates in general to computer systems and databases for managing product data. More particularly, the invention employs computer systems and proprietary databases for gathering, storing, processing and distributing new adverse event data associated with medical and non-medical products, including drugs, medicaments, biologicals, food additives, chemicals and the like, or devices, as well as computer databases for generating, storing, analyzing and processing information related thereto.

BACKGROUND OF THE INVENTION

For several reasons, adverse events associated with medical and non-medical products are greatly understated. As a matter of cost, thorough safety studies are typically very expensive to conduct. In the field of generic pharmaceuticals, for example, the cost of doing safety testing is prohibitive because a manufacturer's survival in the business is based on being a low cost producer. By the time a product becomes generic, safety information relating to the drug has already been generated and shared. Thus, a manufacturer of a generic drug enjoys the benefits of the information without incurring the cost of the original safety studies, and there is no legal or economic motivation to conduct additional studies after a drug goes off patent.

Manufacturers also have little incentive to identify adverse events related to their products. As the number and/or types of identified adverse event increases with respect to a particular product, the product becomes less attractive to consumers and the manufacturer's exposure to potential product liability litigation increases.

The safety studies necessary for medical and/or related products, such as drugs, biologicals, medical devices and cosmetics, to receive marketing approval generally involve relatively small populations of individuals (typically a few hundred to a few thousand, or less), who are observed for relatively short periods of time in prospective randomized studies. The studies generally involve strict inclusion criteria, thus persons in the study often differ in many respects from those individuals who actually use the drug post-marketing. The differences between the safety studies participants and the post-marketing consumers may include age, sex, race, preexisting medical conditions, and use of other drugs or devices. Pre-marketing safety studies are, therefore, a less than desirable means of identifying the full array of potentially adverse product events that may occur in populations of general and specific post-marketing consumers.

Post-marketing safety studies normally involve the voluntary reporting of potential adverse events. However, there is often no way to be certain that all occurrences are reported or, in fact, whether each reported event was caused by the medical product or not. For instance, adverse events generally are reported if they occur within a short time of initiating treatment with a product. Thus, it is difficult for a clinician to link an adverse event to a medical product if the event occurs months or years after it was first prescribed, or even after use of the product was discontinued.

Additionally, when a potential adverse event is something that also frequently occurs in people who have not used the medical product, it is difficult to determine if the medical product may have increased the frequency and/or magnitude of the event. This scenario is problematic because the incidence of such events in a matched control population is often not known. Thus, under normal safety testing conditions, it cannot be readily discerned whether the incidence of adverse events is greater in the group using the medical product versus a corresponding control population. Consequently, since the rate or intensity of an adverse event associated with the use of a product cannot be accurately determined, a reliable assessment cannot be made of whether the risk of using a product exceeds its benefit.

Pre-marketing and post-marketing of medical products is regulated by the Food and Drug Administration (FDA), and manufacturers are required to disclose all adverse events caused by their products. Nevertheless, in the pharmaceutical industry very few, truly comprehensive and detailed studies on adverse events are conducted. Most of the studies are performed by contract research organizations, funded by pharmaceutical companies as part of the FDA-required evaluation. A few government-funded studies may also be performed. However, in general, neither of these sorts of studies detect the frequency of adverse events in specific subgroups, such as those defined by typical demographic factors, e.g., age, race, sex, etc.

Moreover, the data from each manufacturer's study into the potential adverse events resulting from the use of a product is made free to the public, including to competing product manufacturers, and to the FDA. However, because the data is limited, it has in some instances been misused, and sectors of the pharmaceutical industry remain underdeveloped. In other words, some products continue to be prescribed, when they should not be, while other products are not prescribed, when they should be. The result in either case, may be the occurrence of unnecessary adverse events and patient suffering. Accordingly, consumer costs for improperly prescribed medical products is needlessly high, since a manufacturer's cost to produce a medical product, which is passed on to the consumer, includes not only actual manufacturing costs, but also any costs arising from the occurrence of adverse events. For example, some vaccine manufacturers are responsible for compensating individuals who develop unforeseen adverse responses to the vaccine.

Most manufacturers or distributors of products or devices are required by law to warn consumers about potential adverse events, even though this information is generally inadequate as described above. With prescription pharmaceuticals, this information is called "labeling," and is generally included in a "package insert." With industrial chemicals, there is often a "material safety data sheet," also called a "product safety data sheet." Consumer products including foods with chemical additives, over the counter medicines, electronic instruments, machinery or chemicals the information may be inserted in a piece of paper or written on a outer container, such as a cardboard box, or on an inner container, such as a plastic, paper or foil container which holds the drug or medicament. However, the location of the safety information may vary with the product and or industry.

One skilled in the art will know where and how the safety information, is or can be provided by the company manufacturing or selling the product or device. This information can also be termed a "safety data sheet," as a generic term describing safety information included with any type of product or device.

By comparison, proper product labeling discourages those at high risk for an adverse response from utilizing the product, thus decreasing adverse events and, ultimately, the consumer cost of the product. Some factors affecting high-risk use include drug dosing and adverse drug combinations. If consumers are placed on notice through proper labeling, which describes the potential for the occurrence of an adverse event associated with dosage, drug interactions, preexisting conditions and other high risk factors, the number of adverse events is significantly reduced. This decreases the manufacturer's product liability exposure, which ultimately reduces product cost to the consumer. To date, however, there has been no realization of the potential for comprehensive, subscriber-accessible proprietary product safety information, such as a database, to enhance the quality and reliability of adverse event reporting and product labeling.

U.S. Pat. Nos. 5,737,539; 5,833,599; 5,845,255; and 5,908,383 disclose computerized systems for providing patient-specific medical treatment information. The systems enable health care providers, such as medical doctors, to access databases containing pharmacological or other medical information via a computer, and to match a patient's medical symptoms and/or prescription history with known data to produce an appropriate prescription or treatment for the patient. These systems, however, do not analyze raw adverse event data or create proprietary adverse event information based on such data that may be used to identify new uses or restrictions for medical products, or to develop improved packaging or labeling information that accompanies a medical product.

Pharmacoepidemiology is a scientific field pertaining to the analysis of data to test or confirm a specific hypothesis pertaining to an adverse event, and to the utility of a pharmaceutical product. The field has not been utilized in the past for the commercial purpose of generating purified data for the purpose of developing proprietary new uses and kits, wherein the data pertains to discovering previously undetermined adverse events resulting from the use of a product. Pharmacoepidemiology can be performed by analyzing medical records, health care records, such as drug sales or billing information, or by conducting specific surveys based upon relevant questions. Medical records can be reviewed using a computer if the records are in a computer readable form.

Pharmacoepidemiology is a field principally involved in hypothesis testing. It is not designed to commercially develop proprietary new uses for new or existing products. For example, an adverse event may be independently reported by more than a dozen physicians, at which point a group of researchers may perform an epidemiological study to confirm an association among the reports. However, the results are often held in doubt until a second group of researchers performs a study to confirm the findings in the first research report. Sometimes pharmaceutical companies sponsor pharmacoepidemiological studies. However these are usually only performed because a regulatory agency, such as the FDA, has requested the information, after it has received reports of possible adverse events.

After several such studies are performed, a pharmaceutical company may include the results in a package insert. The adverse event information is not, and can not be made proprietary, since the findings are made obvious after one or more physician report the association, and act upon the finding. Confirming the findings by conducting pharmacoepidemiological studies, however simply increases the proportion of users who utilize the safer use, it does not create new uses.

Computerized pharmacoepidemiological studies are performed more frequently in hospital-based settings, in which case all of the pertinent data is likely to be linked by a computer. For example, in such a setting, the laboratory, radiology, discharge reports, and billing statements may all be networked and accessed by computer. Epidemiological studies by computer on outpatients are more difficult to perform, since there are few places where all of the pertinent information is on a computerized system. Medical insurance records may be the most likely the single greatest source of patient information.

However, the process of searching databases in attempt to discover new adverse events has been frowned upon as unreliable. For one reason, based upon current statistical methods, one in every 20 associations that reach statistical significance ($\rho=0.05$) are merely do to chance, alone. Furthermore, a statistically significant association, even if it is not due to chance, is still unable to provide a causal relationship. Confounding variables explain many associations between a product and an adverse event.

In addition to studies conducted by Kaiser and Group Health, extensive computerized pharmacoepidemiology has been performed by groups at the University of Utah (Classen et al., *N. Engl. J. Med.* 326(5):281–6 (1992)), at Harvard University (Brewer et al., JAMA 281(9):824–9(1999)), two or more groups in the United Kingdom (Mackay, *Drug Saf.* 19(5):343–53(1998)), and a few others. None has attempted to purify/transform adverse event information into new adverse event information for the development of proprietary new uses or proprietary kits.

As described by Chen et al. (*Pediatrics* 99(6) (1997)), computers have also been used to verify previously reported adverse events related to vaccines. The VSD project discussed therein promotes utilizing its research in the development and use of safer vaccines. However, it does not disclose the notion of identifying new and proprietary uses for existing vaccines based on the discovery of new adverse events associated with the vaccines. Moreover, the VSD project was unable to discern new adverse events from previously reported adverse events.

Little if any use for adverse event information is taught in the prior art. Classen (U.S. Pat. No. 5,728,385) discloses new methods for administering vaccines, which involved timing of the immunization. The new improved use which related to changes in the timing of dosing, was not directly related to an adverse event but was an new efficacy use, i.e., improvement when given earlier. The improvement, i.e., prevention of a chronic immune mediated disorder was limited to immune stimulants (vaccines) and pertained to autoimmune diseases, allergies, and immune mediated cancers. Furthermore, the '385 patent provided a more efficacious use of the vaccine, i.e., improved protection when the vaccine was administered earlier, and the relevance of age at the time of immunization. Furthermore the analysis in humans did not involve databases where the outcome, chronic immune mediated disorders, were linked to immunization records, nor did it describe screening or determining the potential commercial value of the occurrence of adverse events.

Similarly, improved dosing has been patented, for example the use of taxol (U.S. Pat. No. 5,621,001). The new method of using taxol was not, however, based upon a newly discovered adverse event. Rather, the adverse event, neuropathy, was already known to be associated with use of the drug. The inventors conducted clinical trials to decrease the occurrence of the adverse event, but they did not develop a new use of a product based upon the discovery on a new adverse event, furthermore they had contemplated giving a range of doses to ascertain safety of the product when the original compound and method of use were patented. The simple discovery that one dose may be more efficacious or safer than another dose of the same product, does not result in a new use of the product if it had been previously prescribed at such dosages (Classen et al, *N. Engl. J. Med.* 326(5):281–286 (1992)).

Regulatory agencies do not require new clinical trials to permit a manufacturer to warn of a potential adverse event, even when such adverse events are detected more frequently in certain subgroups. It is considered unethical to perform clinical trials to verify or prove adverse events, since such studies would involve proving one could harm a patient.

Pharmacogenetics and pharmacogenomics are fields dedicated to determining the genetic basis for pharmaceutical phenomenon, such as drug metabolism. For example pharmacogenetics has been utilized to determine why some individuals metabolized a drug faster than another. This approach has been successful when a single enzyme is responsible for the event. Pharmacogenomics is similar to pharmacogenetics, but involves studying the effects of multiple different genes on a characteristic, such as drug metabolism or adverse event. The goal of these fields is to develop genetic tests to individualize pharmaceutical treatment based on a person's genes. However, these fields do not involve screening databases for new adverse events, rather they start with a defined adverse event, and then attempt to determine the molecular cause of the event. If the pharmacogenetic study leads to a new use, that use involves the use of specific laboratory test, usually a molecular test, in conjunction with the administration of the selected drug. In this situation a prospective clinical trial is needed before regulatory approval, i.e., FDA approval, of the new use. Thus, the new use is not the result of the discovery of the adverse event; it is the product of the clinical trial.

Therefore, prior to the present invention, a need has existed for a system for analyzing adverse event data that is associated with a medical or non-medical product, and for creating useful proprietary adverse event information based on the analyzed adverse event data. The present invention meets this need, and is of particular benefit in connection with products already on the market, because there is potentially extensive pre-existing data for such products that may be analyzed for adverse events.

SUMMARY OF THE INVENTION

The invention provides a method, system and article of manufacture by which adverse event information is utilized, for example, to identify new uses for medical or non-medical products or devices, or restrictions that should be applied to their existing uses, or to develop improved packaging or labeling information that should accompany such products or devices. In contrast to the prior art, including the inventor's earlier filed application U.S. Ser. No. 09/449,178 (now allowed), the current invention involves screening raw adverse event databases to discover new adverse events.

In a preferred embodiment, the method comprises steps, wherein one starts with a linked database that contains adverse events linked to exposure to or use of a device or a product, such as a drug, and further to demographic information of the person, such as age, sex, race, height, weight, tobacco use, alcohol use, preexisting medical conditions, use of medicines etc. The database is screened for adverse events associated with the exposure to a specific product. By using this approach one can find many different adverse events associated with exposure to or use of the product or device. The study can be repeated in a different database, for example, in a database comprising different people. One can determine if the adverse event or use is newly described (i.e., new) by searching recognized databases in the art, such as Medline®.

An additional preferred embodiment of the invention provides a system and method of purifying unprocessed adverse event data, which has little if any utility or value in its raw state, and its subsequent transformation through analysis, tabulation, documentation into proprietary data, which can be commercialized in the form of new uses of a product, and proprietary kits containing the data.

The concept of "purification" of data is similar to purification of minerals, wherein the unpurified material is of little value, but the purified material may have great commercial value. Prior to the present invention, those in the art, including pharmaceutical companies did not process the raw adverse event data to provide valuable, proprietary, safer uses of drugs or kits to facilitate such uses. The unpurified data was simply published into the public sector.

The present invention utilizes a computerized system for gathering, storing and processing adverse event data associated with medical and non-medical products to create proprietary databases containing useful adverse event information. The adverse event information may be used, for example, to identify new uses or restrictions for medical or non-medical products or devices, or to develop improved packaging information that can accompany medical or non-medical products or devices.

Moreover, the invention contemplates new uses, which do not require adverse events.

In certain preferred embodiments, the system gathers, stores and analyzes vast amounts of adverse event data regarding a product or device, such as from patients being treated by a particular medical product or device. The system can be used to track essentially unlimited product data. The useful adverse event information contained in proprietary databases may include, for example, catalogs of previously known and newly identified adverse events associated with the product or device. The proprietary databases may be subscriber-accessible for direct release to any persons or entities having a need or desire for the information including, without limitation, consumers, manufacturers, research institutions, health care providers, regulatory agencies and attorneys.

The system preferably also has the capability to format the adverse event information for incorporation into licensing contract documents that may be used in negotiations with product manufacturers and/or distributors. The manufacturers and/or distributors, in turn, may use the information to develop and market new uses for existing products. The information may also be used by the manufacturers and/or distributors to provide improved packaging information that can accompany their products to inform users, consumers or medical product or device prescribers of new uses for their medical products or devices. New uses may comprise restrictive uses coupled with directions or warnings not to use the product or device in certain populations or situations where the system according to the invention identifies the risk of adverse events as being increased. Other new uses may include more expansive uses of the product or device. For example, the new use could be coupled with directions to promote more frequent use of the product in certain populations or situations relative to other populations or situations. In either case, a kit can be produced containing the product or device, and improved documentation providing warning, instructions and/or labeling.

Although not limited thereto, the present invention is especially useful in reducing previously unforeseen adverse events caused by medical products including, but not limited to, drugs, vaccines and non-vaccine biologicals, and medical devices. When the medical product is a drug, the product may be proprietary (e.g., protected by patent) or generic.

For non-drug medical products, such as biological products and medical products, as well as non-medical products, similar products having similar characteristics can be adjudged similarly for their adverse event information. For instance, if a red truck and a black truck would be considered the same product if they are equipped with the same or similar fuel tanks, and if their risk of fuel tank explosions is based on the design of the fuel tank.

For devices, whether medical or non-medical, the same principles apply, and the methods, systems and articles of manufacture of invention are provided.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

DETAILED DESCRIPTION OF PREFERRED EMBODIMENTS OF THE INVENTION

Figure 1:
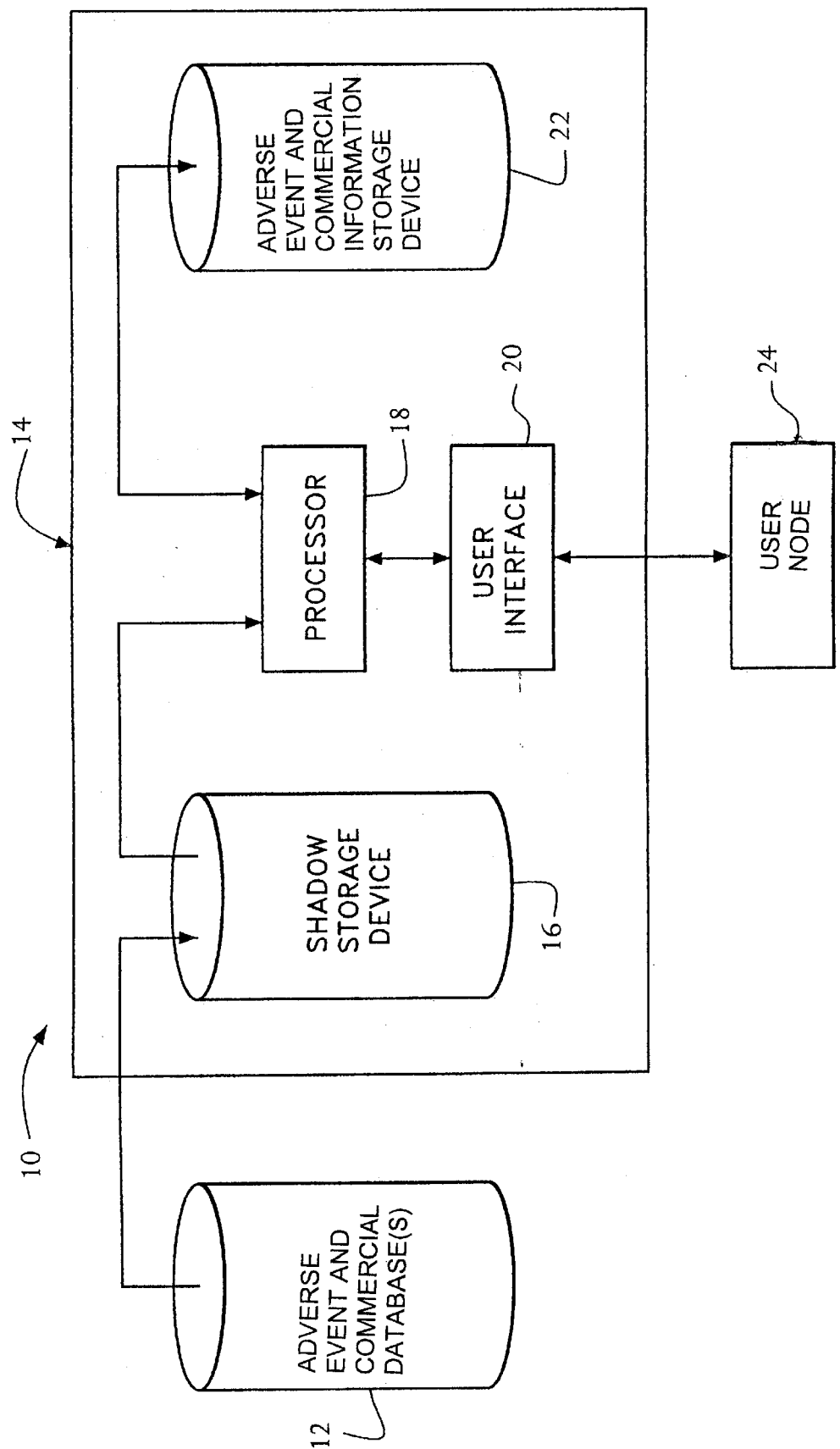
FIG. 1 is a schematic view of a first embodiment of a system according to the present invention.
Figure 2:
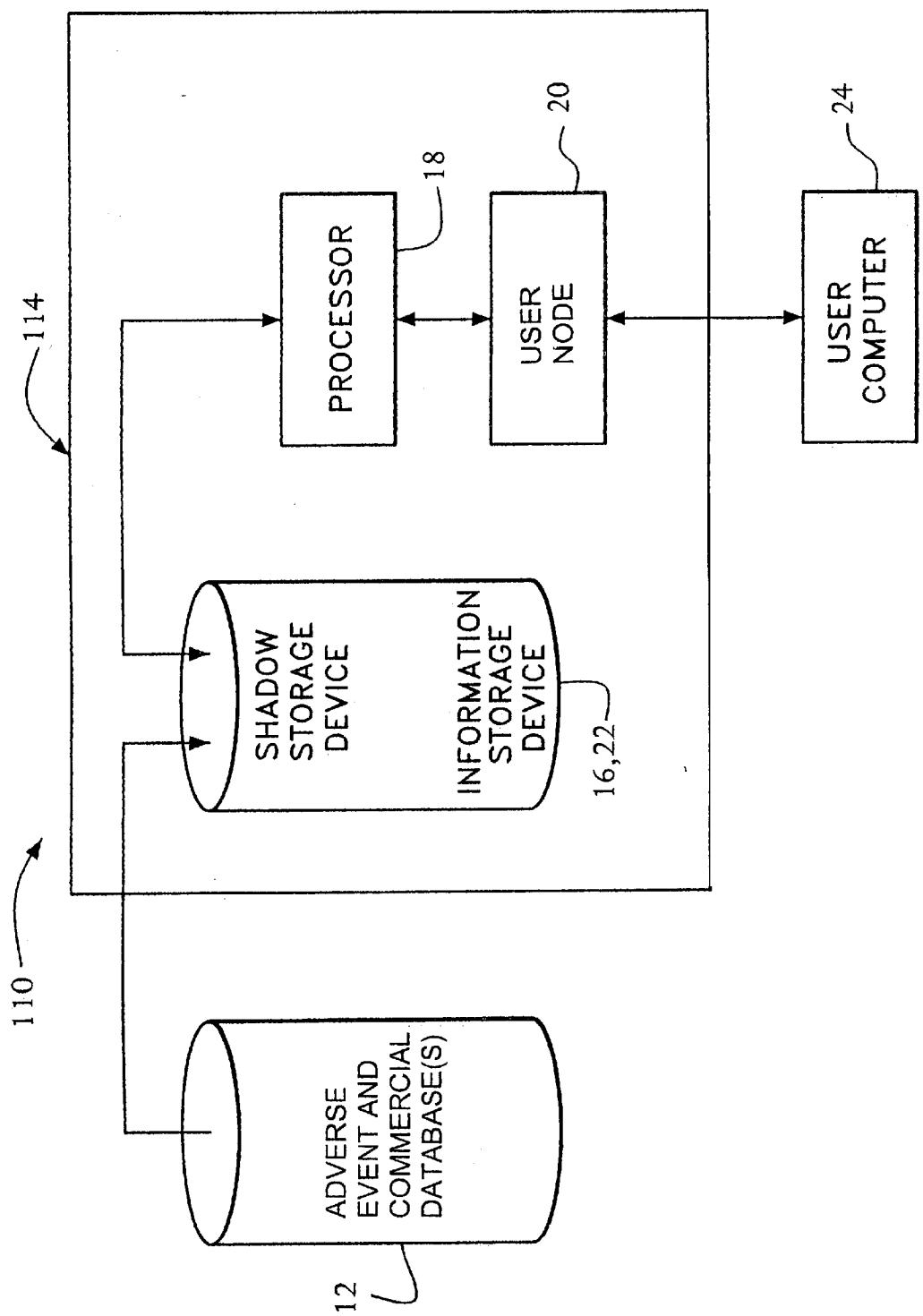
FIG. 2 is a schematic view of a further embodiment of a system according to the present invention.
Figure 3:
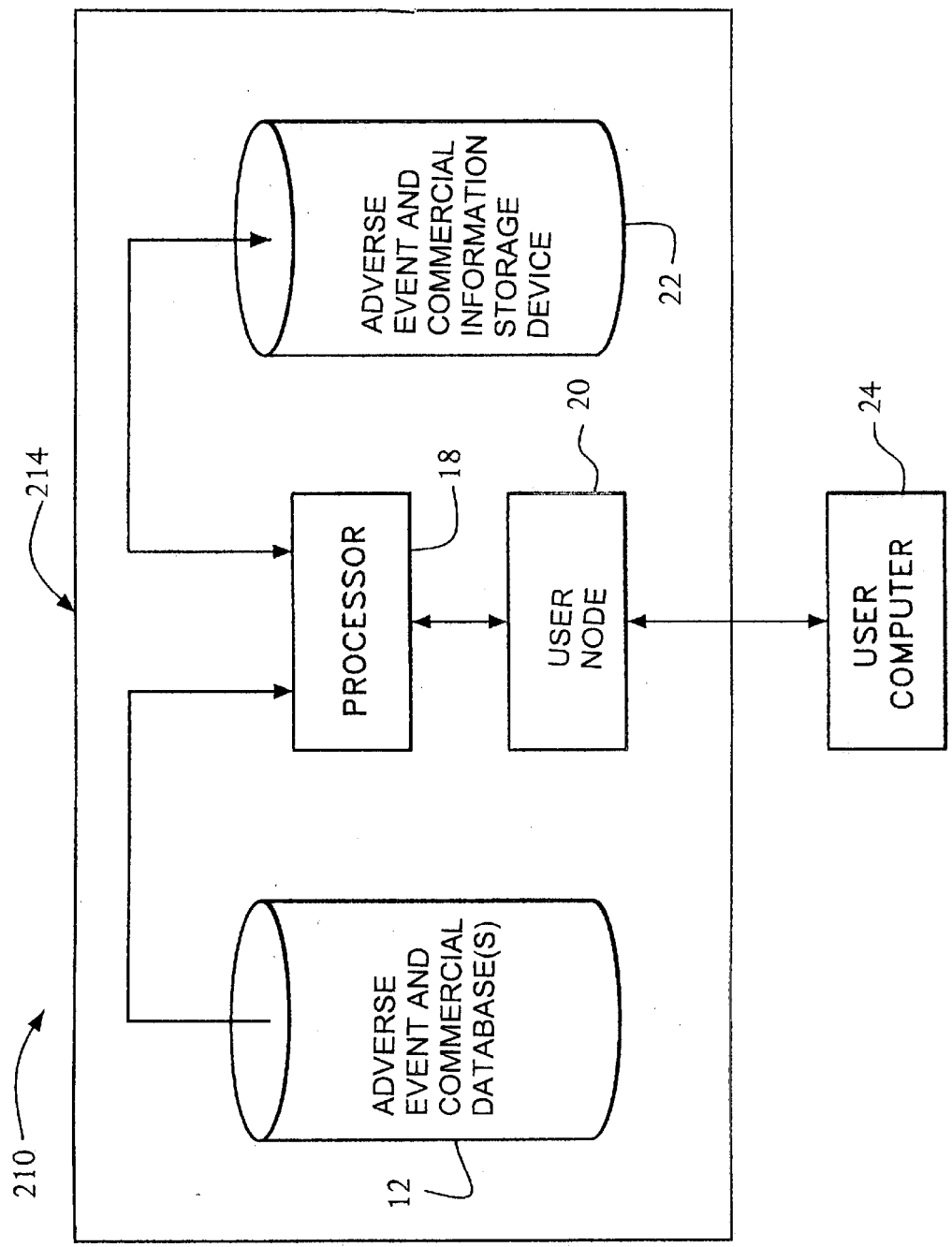
FIG. 3 is a schematic view of a further embodiment of a system according to the present invention.

The inventor's prior invention, U.S. patent Ser. No. 09/449,178 (now allowed) describes a computer system and method for deriving new uses based on new adverse events, which also finds application in the present invention. However, the currently embodied system and method of the invention provides advances over that invention. Referring to the drawings, wherein like references indicate like elements throughout the several views, there is shown in FIG. 1 a first system 10 constructed in accordance with the present invention. System 10 includes at least one adverse event and/or commercial database 12 and a server. Depending upon the source, the adverse event and/or commercial database(s) 12 may be accessed by server 14 free of charge or for a fee. Adverse event and/or commercial database 12, preferably contains large amounts of data regarding a particular medical or non-medical product or device. Adverse event data and the commercial data regarding a product or device may be found on the same database, as shown in FIGS. 1–3, or on separate databases (nor shown), or in a combination of both.

The term "product," as used herein, means medical or non-medical products, and is expressly intended to include "devices," whether stated or not. The more narrow term "medical product" as used herein means drugs, vaccines, non-vaccine biologicals, medical devices and any other medically-related goods and therapies. Drugs and biologicals as the terms are herein used within the term "medical product," are intended to encompass any known, or as yet unknown, class of drug, medication or biological therapeutic (including inhibitors, preventors, enhancers activators, stimulants, catalysts, promoters, regulators, and the like). These can be categorized by their effects on an organ system, such as cardiac, respiratory, renal etc. Drugs and biologicals are also be classified by their chemical composition, e.g., sulfa drugs, penicillin derivatives, vaccines, immune stimulants, antibiotics, etc. In addition, they can be classified according to their activity, e.g., diuretic, antibiotic, beta blocker, and the like.

Medical devices can be similarly classified by those of ordinary skill in the art, e.g., medical devices may be grouped as defibrillators, EKG machines, infusion pumps, CT machines, etc. To further assist in the categorization process, those skilled in the art may consult medical science resources, such as medical libraries or online authorities, such as Medline® and the like to locate articles, books or other printed or electronic publications on the subject of interest, such as the non-limiting example of Goodman and Gilman's "The Pharmacological Basis of Therapeutics."

"Non-medical product" as used herein is construed to mean any non-medically-related product or device that may cause harm to a consumer including, without limitation, foods, food additives, beverages, vitamins, alcohol, tobacco, cosmetics, mechanical devices and children's toys, personal and household cleaning products, and other chemicals, such as paints and related coatings, insecticides, herbicides and industrial chemicals.

Because of the large volume of data that they contain, preferred adverse event databases may include those of medical insurance companies, managed care organizations, pharmaceutical and medical device manufacturers, public health departments, hospitals and the like. Typically, each adverse event recorded in such databases links the adverse event with demographic information, such as the age, sex and race and, frequently, one or more physical condition factors of the individual that experienced the adverse event. The result is that adverse event and/or commercial database 12 may contain thousands or even millions of items of data. Such vast repositories of information enable the data to be analyzed to generate statistically relevant and reliable information relating to age, gender, racial, physical condition or other subgroup.

The databases most useful for the discovery of new adverse events and new uses based on the new adverse events will depend on the product or device class (for example, drug, medical device, non-medical product or device and the like). For example, a drug adverse event can be discovered using a database of medical records. An adverse event related to a car, for example a faulty tire, may be detected using auto insurance databases. An adverse event pertaining to an industrial product may be detected by looking at health insurance databases or databases pertaining to life insurance, as a non-limiting example. One skilled in the art will know what type of database will be suited for determining the new adverse event.

There are several types of databases that can be useful for determining the potential commercial value of a new adverse event and its related new use. Production databases include information related to the production of a product, including production costs, sources of raw material, contract manufacturers, costs of supplies, and the like. Regulatory databases include information regarding the laws pertaining to the manufacturer and sale of a product. In fact, specific databases exist for every facet of developing, producing and marketing of a product or device, and such databases would be known to one of ordinary skill in the art.

"Separate databases" refer to those databases which contain different information. For example, one medical database may include the medical records of those individuals covered by one insurance company, while another database may include medical records of people covered by a different insurance company. There may be overlap since some people may have insurance coverage with both companies, or they may have switched coverage from one company to another, and as a result they are identified in each. Moreover, databases are generally created by different people or entities. For example separate databases of reported or previously known adverse events can include patent databases, Medline®, databases of reports to the FDA, and the like. Accordingly, one can combine information from several databases to create a list of all reported or previously known adverse events. However in this situation, such a compilation would represent more than one database.

In some cases several different and/or separate types of databases may be employed to analyze information and events relating to a particular product or device. For example, databases from both medical records, workman's compensation, and life insurance may be used for determining an adverse event due to a toxic substance used in a work-related contact with asbestos. Therefore, one must consider the type of product being studied, the type of information stored in the database, and any specific adverse event one is looking for to determine if a database will be suitable to provide the information needed.

In a preferred embodiment, one of the databases includes reported or previously known adverse events relating to the use of or exposure to products or devices. These represent "old" adverse events known to have occurred in association with the product or device. By comparison, in order to determine a "new" adverse event, one must define what has been previously known and is in the public domain. The phrase "reported or previously known" implies adverse events that are in the public domain, and to that extent are unpatentable. Not all adverse events known to those practicing the art, such as a physician, have been reported in the literature or to a company or regulatory agency. However, these events are also not patentable, if they are known within the community of those skilled in the art.

Returning to the diagrams of the system, server 14 preferably includes a shadow storage device 16, a processor 18, a user interface 20 and an information storage device containing compiled adverse event and/or commercial information. Shadow storage device 16 gathers and stores adverse event and/or commercial data received from the adverse event and/or commercial database(s). Processor 18 may be any computer processing means suitable for executing the operations of the present method as described hereinafter. User interface 20 may include any suitable input/output (I/O) equipment. Adverse event information storage device 22 stores adverse event and/or commercial information that is generated by processor 18 responsive to analysis of the adverse event data stored in shadow storage device. The shadow and adverse event information storage devices 16, 22 may be any memory devices capable of storing large amounts of information. Lastly, system 10 includes a user node 24 for interfacing with user interface. User node 24 is preferably any commercially available personal computer, computer terminal, workstation or the like which can exchange information with user interface 20 in the manner well known in the art.

If the event data relating to a medical product is desired, the adverse event data in adverse event and/or commercial database 12 can be collected using the ICD and other disease codes on admission, discharge, pharmaceutical sales, physician visit records or other known sources. The systems of the present invention may also accommodate and process animal safety test data, such as animal toxicity data.

Preferably the new (safer) use, derived from the new adverse event, involves screening human and veterinary subjects for high risk of developing an adverse event following exposure to the product or device in question, and then substituting the product with a different product (i.e., drug) or method (i.e., surgery, device). Preferably the screening is performed objectively based on an oral history, records or physical exam, without the need to perform expensive additional tests, such as genetics screening. Additionally, the new use does not require the performance of expensive clinical trials before the FDA allows the information into the package insert. While use of additional tests to enhance a drugs outcome, such as molecular/genetic screening, generally requires addition clinical studies, the inclusion of new adverse event information does not.

Preferably the new use is more than a simple optimization of dosing or changes to the timing of the dosage.

Through operation of system 10 and the other systems described herein, the data extracted from the adverse event and/or commercial database is analyzed by suitable programming of processor 18 to produce useful adverse event and/or commercial information that is storable in an information storage device. For example, the adverse event database may store information on frequency of adverse events, such as death, hospitalization, office visits, disability, missed work, medical costs, abnormal lab results and surgeries in individuals receiving the medical product in question and this information can be compared to the observed adverse event rate in the same persons before receiving the medical product or in persons of similar characteristics (i.e., a control group). The analysis can be performed on different exposure rates including, but not limited to the amount, duration and timing of exposure to the product.

The "adverse events" can include damage or alteration to any organ system, including the non-limiting examples of cardiac, respiratory, gastrointestinal, endocrine, muscular, skeletal, liver, renal, spleen, neurological, skin, blood, immune, bone marrow and the like. These adverse events can include the development of new diseases, including the non-limiting examples of seizures, cancers, heart disease, arrhythmia, autoimmune disease, allergy and the like. Moreover, failure of a person to respond beneficially to a drug can also be considered an adverse event.

The adverse event may differ in different industries as described in the following non-limiting examples. In the chemical industry, an adverse event may include an explosion or fire with a combustible product. It could include the tendency of the product or device to interact with certain other chemicals, such as a solvent dissolving a plastic container, or a car fluid causing corrosion to aluminum car parts. With a machine, the adverse event could include failure in extreme temperatures, for example, rocket boosters could fail on the space shuttle, or an automobile could suddenly shift gears while in park.

By "subject" or "patient" of the invention is meant mammals (including humans), fish, and avians; more preferably to veterinary animals and livestock (including cattle, horses, swine, sheep, goats, etc.), household pets (cats, dogs, canaries, parakeets, etc.), laboratory animals (e.g., mice, rats, rabbits, other rodents, primates, etc.), fish (especially in an aquarium or aquaculture environment, e.g., tropical fish, goldfish and other ornamental carp, catfish, trout, salmon, etc.) and avians, especially poultry such as chickens, ducks, geese, etc. Most preferably the terms refer to humans. Occasionally the term "user" or "consumer" is substituted for these terms. When the term "person" or "individual" is used herein, it is to be construed broadly to also include animals, fish, fowl and the like, as described.

The database to be screened for new adverse events may include adverse event information relating to the use of products in, or devices on, humans, animals, etc. While human data is more valuable for determining new uses of a product or device in humans, it is possible that new adverse events detected in animals can be used to develop new product characteristics or uses in humans. For example, detection of birth defects, or drug interactions in animals may lead to new uses comprising restricted use in pregnant humans or humans taking certain drugs.

Databases of adverse event information can be created by screening animal models of specific human diseases and cell culture models of human diseases for the potential new adverse events. In this situation an animal model of human disease is exposed to the product and the frequency or severity of the disease is recorded compared to a control group. Ideally the product or device is exposed to as many different animal models of human diseases as possible or feasible.

In a similar manner, a culture of cells can be exposed to a product in many instances. This is easily accomplished if the product is a drug, chemical, or emits radiation or comprises a marker. The cells may be normal cells, premalignant or malignant cells. One can compare the outcome of using a product on the cells, to that of the effect on control cells. Endpoints include the non-limiting examples of cell death, cell mutation and cell division and the like. Ideally, the product or device is exposed to as many different animal models of human diseases as possible, or as economically feasible.

One can use the data from the database to compare to previously known adverse events to determine new adverse event information. The order by which one checks for an adverse event can vary, and any order that is suitable is acceptable. For example, one can hypothesize that a product causes one or more adverse events. One can then analyze raw data to see if the product causes an adverse event, and then determine if the adverse event is new. Alternatively, one can hypothesize that a product causes an adverse event, and then check databases to see if it has been reported that the product is associated with the adverse event. If the association has not been reported, then one can screen raw adverse event data/databases to see if the product is associated with the adverse event. If data does not exist to test the hypothesis using available raw adverse event data, then new data can be generated in the form of a study. In most cases, this would involve animal toxicity studies since performing prospective studies in humans to prove adverse events is generally unethical.

By "raw data," as used herein, means data before it is processed and analyzed. For example, the raw efficacy or adverse event data relating to a drug would include all of the collected data, which is linked to individuals who used the drug, or in some instances for a product such as tobacco, for those exposed to the product. This raw data could include, e.g., the individual's weight, height, race, lab results, medical conditions and length of use or exposure to a product or device. By contrast, "processed data" means analyzed data that has been categorized or qualified to meet the requirements or standards of a particular situation.

For example, processed data may only include a summary of the raw data, such as a statement that a drug reduced the risk of death by 30% without details of how the results were obtained or what other factors may have added variability to the outcome of the analysis. The processed data usually does not contain sufficient information to do a thorough subgroup analysis. The subgroup analysis is helpful in developing new uses for a product or device, e.g., determining whether information regarding the occurrence of an adverse event exceeds the benefit in certain subgroups, such as those older than 65, those under age 5, persons of certain racial groups, those with certain diseases, or the like.

Raw data also pertains to commercial data. "Commercial data" is information pertaining to the ability to profit from the sale or trade (as opposed to the use of) of a product or device. Commercial data is not intended to mean, e.g., what drugs and amounts of drugs a person is taking. Nor is it intended to mean, e.g., what number or percent of people are taking a drug, such as insulin, as additional information is needed to estimate profitability, such as unit costs, sale prices, competitors, market share, etc. Raw commercial data provides a wealth of information that can be used to assess the potential commercial value of an new adverse event and the related new use. For example, the raw data may indicate certain markets that are extremely profitable or show growth potential.

A product or device may be distributed or sold for several indications, many of which may offer a low profit margin, e.g., in the situation in which competition is high, or when the buyer has a monopoly and can control prices. In contrast, processed data may include yearly sales. In many cases, processed data comes from company annual reports or SEC filings. They may include the yearly sales. Even when profits are reported, it is difficult to determine the true profit from the sale of a product. This is because the cost of a product or device includes fixed costs, such as administrative costs, fiscal costs and costs of production.

Raw commercial databases can include clients who are willing to pay premiums for a product because they need or desire a higher quality, or a product that better fits their needs. Also the raw data may include those clients with both good credit history, and those with bad credit. Raw commercial data will thus help determine if a new adverse event and its related new use or characteristic are of potential commercial value.

In preferred embodiments, system and method are provided, wherein existing raw adverse event databases are searched for adverse events, then determinations are made as to whether the discovered associations are new. An additional study can be performed to verify the finding. In another preferred embodiment, one can hypothesize about certain adverse events, and then determine if those events have been previously reported. If they have not, then one can analyze raw adverse event data to determine if there is an association.

Additional adverse event information may also be derived from subgroup analysis. Subgroup analysis can be performed to determine specific high risk groups who may be at increased risk of having an adverse event. Subgroups can include persons with similar characteristics, such as sex, age, race, weight, height, percent body fat, genetic characteristics, pregnancy status, allergies, additional medical problems, use of additional medical products (including devices), past medical history, family history, social history, occupation, use of alcohol, tobacco, recreational drugs, and history of abnormal lab tests, such as EKG, chest X-ray, liver function test and kidney function test. Preferably this demographic data, i.e., subgroup information, is available through personal history and physical, where no additional laboratory test is needed for a new use. The subgroup analysis can include groups that were not represented or were under-represented in safety studies that were required for marketing approval or were done around the time of market introduction. For example, a drug may be approved for use in persons over the age of 18. However, people under 18 may also receive the drug. In such case, packaging for the drug may not include sufficient warnings for persons under 18, in general, and subgroups of persons under 18, in particular, that are at greater risk of adverse events linked to usage of the product or device.

Ideally, systems according to the invention can track large numbers of variables to locate groups at high risk of adverse events. As a non-limiting example, the systems could be configured to track people taking multiple different drugs (2 together, 3 together, 4 together, 5 together, and the like) to determine whether a toxic adverse event occurs in people taking 2, 3, 4, 5 or more, or all of the drugs, at once. The systems may utilize statistical formulae to identify groups at high or low risk of adverse events. Preferably, a database of adverse event information associated with a product or device contains data regarding a plurality of different adverse events, and it is not limited to a single type of event, such as diabetes, birth defects or the like.

Studies, as described above, and in other sections of this document, however, do not necessarily prove that a product or device causes an adverse event, only that the adverse event and the product or device are associated. In some instances there may be a direct link. For example, wealth or standard of living is associated with certain adverse events. Money does not cause the adverse events, but it allows wealthy individuals to buy products that cause a specific adverse event. If an epidemiology study does show an association between an adverse event and a product or device, then there is a risk that the associated product or device caused the adverse event.

This risk exists even if the association is not statistically significant. However the risk is greater if a statistically significant association exists. Since some of the associations are true causal relations, knowledge that a risk exists has utility since one can take steps to avoid the risk, when one knows that it exists.

The systems and methods according to the invention may also optionally collect and analyze efficacy data, i.e., data on the beneficial attribute of a product. For example, the benefit of a medical product in certain subgroups can thus be measured by observing the frequency of the intended benefit, (e.g., decreased death, stroke, kidney failure, and the like). Benefits can also include reductions in costs where the costs may include, without limitation, costs of the medical product, medical expenses, lost productivity and the like. By using the data from the risks and benefits, one can determine the risk/benefit ratio for persons in any particular subgroup.

This information can be highly stratified to enable, in addition to previously known uses, new, different or more precise uses for a product or device. For example, a dose of a drug or biologic, the frequency or manner of use of a device, or the setting of a device, such as a pacemaker, may be precisely prescribed to accommodate the individual needs of particular subgroups.

Targeted searches can be performed and their data analyzed by the systems of the present invention. For example, if it is discovered from one adverse event and/or commercial database 12, that persons receiving a medical product are at increased risk of dying of liver failure at a certain dose of medication or when taking the drug in combination with other drugs, then one can attempt to verify the findings using a second adverse event database. Adverse event data from any adverse event data source can also be confirmed in animals or by clinical trials in humans. Targeted searches can also be done following case reports of adverse reactions, discovery of adverse events in animals, adverse events discovered in similar products or devices, and possible adverse responses found in small studies.

An "experimental study" or "clinical trial" is one in which one actively performs an experiment by exposing an effective number of patients, consumers or other users to a product or device, in which they use the product or devise in a method that is thought to induce an adverse event. For example, in the later case, a product could be exposed to heat to determine if it will burn, or exposed to stress to determine if it will fail. An effective number of subjects in a study would be known to those skilled in the art to be quantitatively and statistically representative of some portion of the population. Physical modification of a product would include, e.g., reformulation or changing the physical attributes or characteristics of a product. This is in contrast to changing the safety notices or warnings and instructions for use which accompany the product to instruct the user of the product as to its use. Governmental regulatory agencies often regulate the instructions for use and warnings that accompany a product. One skilled in the art will know whether by law a new use based on a new adverse event will require an experimental or clinical study to verify the adverse event to test the new use, or whether such testing will not be needed.

Consistent with the invention, any number or variety of proprietary databases may be storable on an information storage device. For instance, a first proprietary database can be created containing information about a particular product's or device's adverse events and, optionally, risk benefits and cost benefits of the product or device. The data from that database can be crossed, linked or compared with a database of knowledge already accumulated on the product that may also be stored on adverse event information storage device. Sources of prior known adverse events can include package inserts, the Physician's Desk Reference, The Merck Manual, data from regulatory agencies, such as the FDA, and published literature found on databases, such as Medline®. In the future it is contemplated that databases of patents and patent applications will also contain known adverse events.

New findings on adverse reactions can thus be determined through appropriate comparison and/or interpretation of the databases.

The newly derived knowledge can include, without limitation, catalogs of new adverse events, specific frequency of adverse events, drug interactions and side effects in specific subgroups, such as those mentioned above. For instance, a new adverse event can mean a newly discovered adverse reaction, such as the discovery of an increased rate of seizures associated with a drug, improved information, such as more accurate calculation of the rates of seizures in a group or subgroup, or the discovery of an increased rate of seizures in patients taking the drug along with one or more additional drugs.

Returning to the drawings, FIG. 2 represents a further preferred embodiment of a system according to the invention identified by reference numeral 1. System 110 is constructed and functions substantially similarly to system 10 of FIG. 1, with the exception being that the shadow storage device 16 and information storage device 22 of system 10 are integrated into a single shadow storage device and information storage device 16, 22 on server 114.

FIG. 3 represents a further preferred embodiment of a system according to the invention identified by reference numeral 2. System 110 also is constructed and functions substantially similarly to system 10 of FIG. 1. However, unlike systems 10 and 110, system 210 draws its raw adverse event and/or commercial data from an internal, rather than an external source; that is, server 214 of system 210 directly supports adverse event and/or commercial information database(s). System 210 graphically depicts a situation wherein a holder of a substantial body of adverse event data may itself analyze such data using processor 18, and create one or more adverse event and/or commercial information databases that may be stored on information storage device 22.

Exemplary users of system 210 may include, for example, medical insurance companies, managed care organizations, pharmaceutical and medical device manufacturers, public health departments, hospitals and the like. Although illustrated as separated devices, it is also contemplated that adverse event and/or commercial information database(s) 12, and adverse event and/or commercial information storage device 22, may be integrated into a single storage device, or they may each be a plurality of interconnected nodes.

Figure 4:
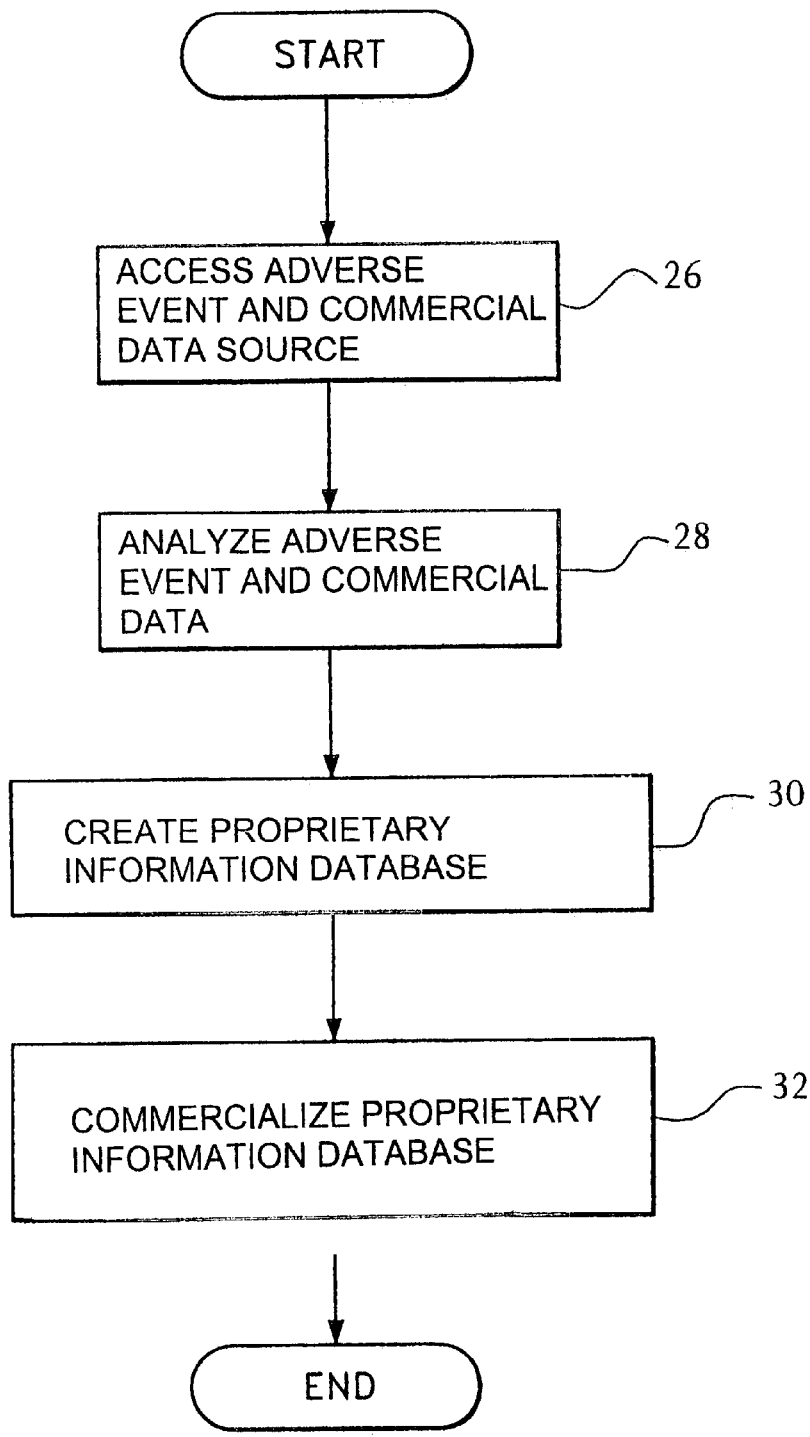
FIG. 4 is a flow chart illustrating the method according to the present invention.

FIG. 4 is a flow-chart that embodies the essential method steps of the present invention that are executed by each of systems 10, 110 and 2 At step 26, the adverse event and/or commercial information database(s) 12 are accessed by server(s) 14, 114, 214 (at a fee or free of charge) to obtain desired data therefrom. In systems 10 and 110, the adverse event and/or commercial information database(s) 12 are external to the servers 14 and 114. Hence, servers 14 and 114 desirably store the data received from database(s) 12 in shadow storage devices. Server 214, by contrast, accesses its internal adverse event and/or commercial information database(s) 12 for the desired data.

The desired adverse event data having been accessed, the processor 18 of systems 10, 110 and 210 then analyzes the data, as described above, to identify previously known and new adverse events, as indicated at step 28. At step 30, the processor 18 further processes the analyzed adverse event and/or commercial information data to create useful proprietary information, such as any of the kinds mentioned above. More particularly, in creating the proprietary information database at step 30, processor 18 preferably possesses logic, whereby it categorizes the newly-discovered adverse event(s) associated with a particular product that are identified at step 28, and also identifies at least one new use for the product responsive to the identification of at least one new adverse event(s) associated with the product. The processor 18 then stores the adverse event information as one or more databases in information storage device 22.

According to presently preferred embodiments of the invention, the data retrieved from adverse event and/or commercial information database(s) 12 is processed and analyzed by a centralized processor 18 on server 14, 114 or 214, and the analyzed data is stored at an information storage device also supported by server 14, 114 or 214. Alternatively, the proprietors of servers 14, 114 or 214 may license proprietary software to users of node 24 that may perform the functions of processor. Such software may be loaded onto the user node 24 to execute the adverse event data analyzing and other processing functions of processor 18 described above, and the generated useful adverse event information may be stored at the user node. In any case, servers 14, 114 and 214 can be directly connected by a user interface 20, such as a modem.

It will be understood that the servers 14, 114 and 214 may also be indirectly connected to a user node 24 via one or more other servers, a central computer or other system designed to link computers, nodes or other processing machines. Ideally, the information should be transferred digitally between servers 14, 114 and 214 and user node. Alternatively, however, it can be transmitted in analog form by a modem along standard telephone lines. It will be further understood that the information can also be transferred by disk, CD-ROM or other electronic media, or printed and then scanned in, or alternatively, manually re-keyed.

Preferably, the user node 24 and associated printers (not illustrated) are sufficiently sophisticated to organize and print all information generated by the systems 10, 110 and 210 in virtually any desired format and on essentially any desired printable medium that may be printed by the printers. However, certain product labels and package inserts that incorporate the information can be manually type faced using type-setting or other conventional printing techniques. The system may also format the data for submission to regulatory agencies, such as the FDA.

The proprietary information that may be generated by systems of the present invention is superior in many ways to the limited, and generally static, adverse event data and databases heretofore known in the art. In respect to medical products in particular, the volume of data and the degree to which the data may be stratified and studied, the systems according to the invention far exceed the capabilities of FDA-required pre-marketing studies for medical products. To illustrate, a typical FDA pre-marketing study generally involves study populations of less than about 5000, and normally less than about 2000 participants. In contrast, the adverse event data that may be amassed and analyzed pursuant to the invention may comprise information on far larger numbers of people receiving the medical product.

Representative populations studied using preferred systems of the invention, in virtually all practical medical product scenarios will generally represent populations of at least 5000, and can be analyzed in any desired increment, such as, for example, 5,000; 10,000; 50,000; 100,000; 200,000; 1 million subjects, or more. However, events related to orphan drugs or products used by very few consumers, the representative population could be as low as 10–50, or 100–500, or up to 1000, or up to 5000 individuals or subjects.

The systems of the present invention will additionally provide a better appreciation of delayed or latent adverse events caused by, or related to, products or devices long after initiation of treatment, or after treatment has been discontinued. Using the present systems, post-exposure follow-up of a product or device can be analyzed in any desired increments of time. For instance, selected post-exposure study periods may be as brief as a few minutes or hours to considerably lengthier periods, such as 1 day, 2 days, 7 days, 10 days, 30 days, 90 days, 180 days, 1 year, 3 years, 5 years, 10 years, or more.

Risk/benefit analyses may also be readily performed using the methods and systems described herein. Acceptable adverse event thresholds may be established and studied for a product or device. The adverse event thresholds may be selected to be at any desired incidence level, e.g., 1:10,000,000; 1:1,000,000; 1:100,000; 1:10,000; 1:1,000; 1:100, above which use of a product may exceed its benefit for a general or specific population group. The adverse event thresholds serve as limits for single or aggregated newly discovered adverse events. For example, an adverse event threshold of 1 occurrence in 1000 persons may be established as an acceptable level of occurrences.

If 2 or more occurrences, preferably independent occurrences, are observed in the target population, then the adverse event threshold is exceeded, and the product or device may be deemed unsafe or commercially impractical for use by persons in that group. Likewise, 10 new similar or dissimilar adverse events relating to the product or device may be observed in the target group, but none of the individual new adverse events occurs more than once in 10,000 persons. In the aggregate, therefore, the 10 occurrences detected in a total study population of 10,000 persons corresponds to a ratio of 1:1000 which equals, but does not exceed the acceptable adverse event threshold for the product under scrutiny. In this instance, the product or device would be deemed safe and commercially viable for use in the targeted population group.

In the event of a death associated with trial of a new and controversial drug or process, such as gene therapy, one such adverse event would be considered a significant adverse event, in even a very small population of patient. By comparison, a large number of adverse events had to be recognized before the risk of using the drug fenfloramine was considered to be significant when viewed in a large population of subjects.

The present systems and methods also enable ready comparisons between target populations that receive treatment with a product or device, and experience an adverse event, and untreated control groups that experience similar adverse events. For example, a target group treated with a certain vaccine, wherein a substantial number of patients from within that group acquires diabetes, may be compared with an otherwise identical, but unvaccinated, control group, wherein a significantly lower number of patient acquires diabetes. Increased incidences of diabetes in the target group, thus would be evaluated as attributable to the vaccine.

Systems 10, 110 and 210 may programmed to establish any desired acceptable increased rates of adverse event occurrences in the treated target group versus the untreated control group, e.g., 2%, 5%, 10%, 20%, 30%, 50%, 75%, 100%, 150%, 200%, 300%, 400%, 600%, 800%, 1,000% or more, above which treatment would be contra-indicated in the target group. Preferably, the system can analyze data using any desired study design. For example, a case control study design may be used where the frequency of using a product in a group with the target disease is compared to the frequency of using a product in a group of controls. The studies may include prospective clinical trials and retrospective follow-up of clinical trials, as well as cohort analysis of people not in clinical trials. The studies may or may not include efficacy for the intended use as in treatment of a specific disease. The studies may also be part of a pre-approval or post-marketing study regulated by the FDA or similar regulatory body. Conversely, the studies may be unaffiliated with FDA-sanctioned clinical trials.

However, there has been no previous attempt in the prior art to screen the adverse events to determine the potential commercial value of a specific adverse event and a product or device which has been used according to a new used responsive to discovering a new adverse event associated with pre-existing usage of the product or device. Furthermore, in no prior database or system has there been a reported connection with a commercial database comprising information relating to the marketing, sales or profitability of the product or device, or to other purely business- or commercially-oriented data.

Returning to FIG. 4, the adverse event and/or commercial information stored in information storage device 22 is commercialized. Commercialization of the useful adverse event information may take on an assortment of forms as indicated in FIGS. 5 and 6.

Users of systems 10, 110 and 210 may include individuals, a corporation, partnership, government agencies, research institutions or any other persons or entities that may have an interest in, or need for, new and useful adverse event information. Non-limiting examples include manufacturers of medical products, insurance companies, health maintenance organizations and public health departments. In the case of manufacturers and/or distributors of medical products, such manufacturers and/or distributors may use the information in the manufacture and/or distribution of their own products, or may license the information to their competitors.

Figure 5:
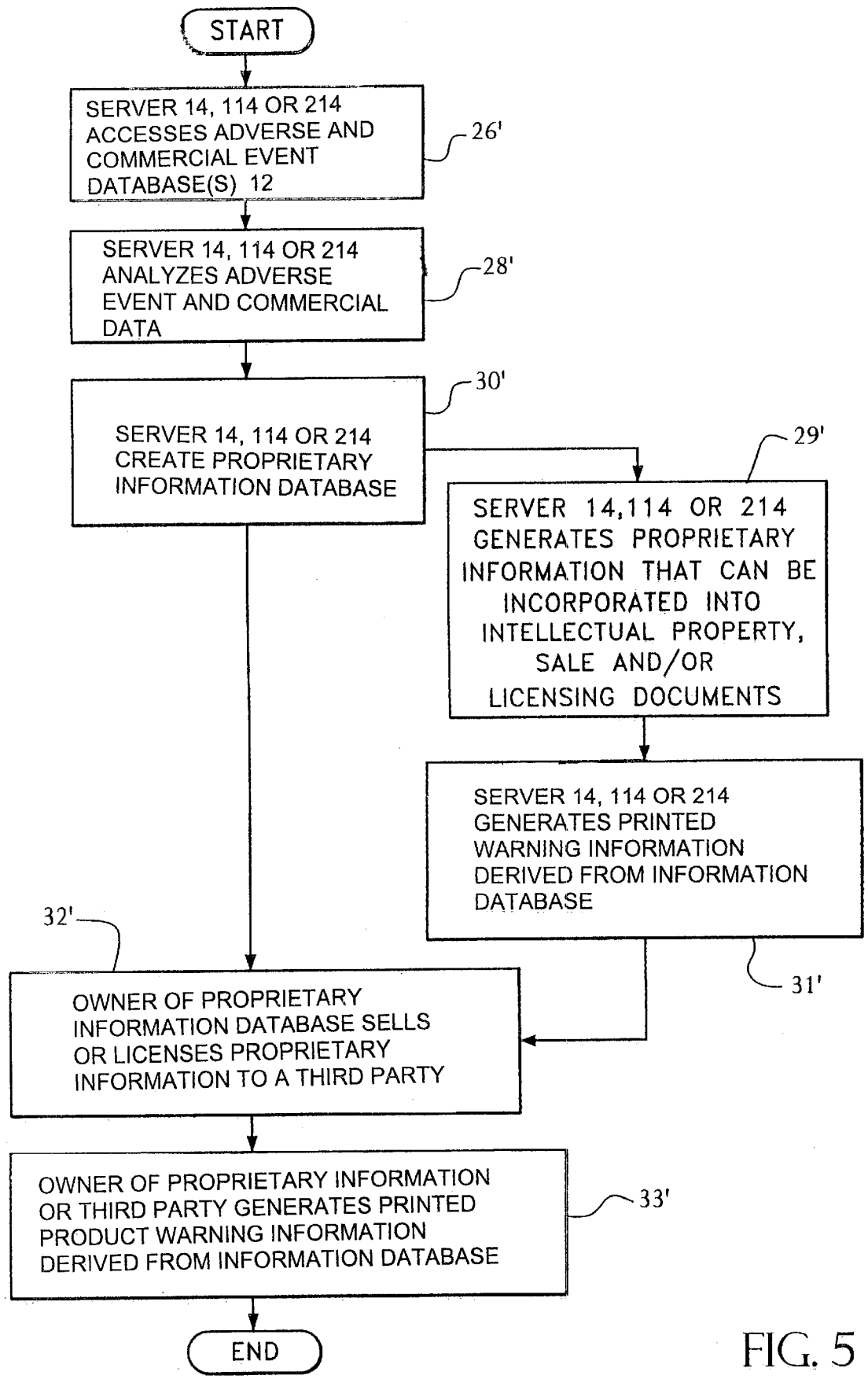
FIG. 5 is a first preferred specific application of the method represented in FIG. 4.
Figure 6:
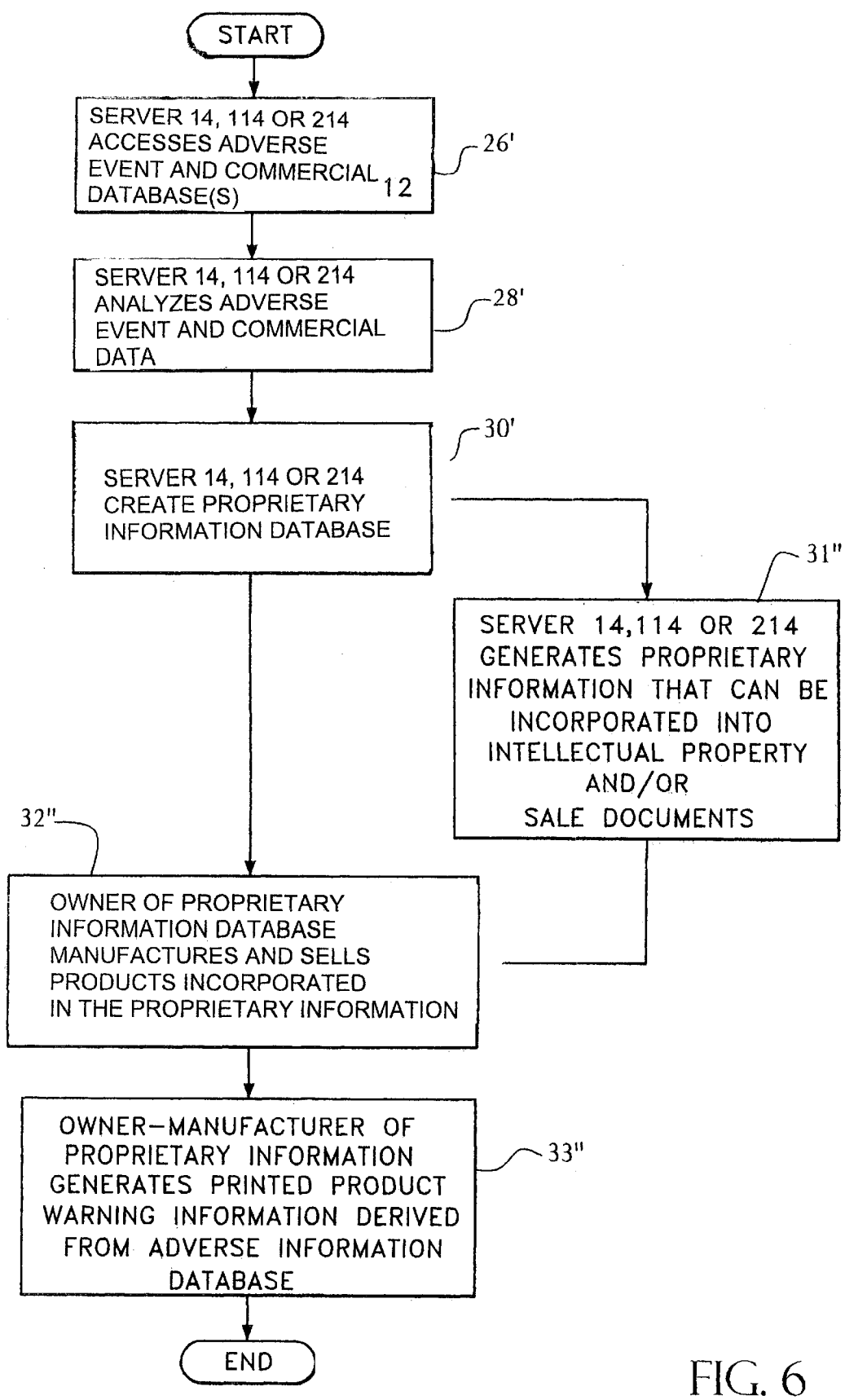
FIG. 6 is a further preferred specific application of the method represented in FIG. 4.

As indicated by step 26' in FIGS. 5 and 6, at the request any of these persons or entities or on its own behalf, the owner or licensee of server, 14, 114 or 214 accesses and retrieves raw adverse event product data from adverse event database(s). At step 28' the server analyzes the retrieved data to identify new adverse events regarding a product, to conduct cost/benefit analyses related to the newly discovered adverse events or to perform any other desired analysis of the raw data. At step 30' the server creates one or more proprietary information databases that are stored in information storage device. At step 32' in FIG. 5 the licensee or owner or owner of server 14, 114 or 214 commercializes the proprietary information in the information storage device 22 by selling or licensing the proprietary information to a third party. The third party communicates with system 10, 110 or 210 through user node. The user node interfaces with user interface 20 to make requests for information to, and to receive information from, the processor 18 of server 14, 114 or 214. Interpretation of the received information may be performed by the third party, an independent contractor, the owners or licensees of server 14, 114 or 214 or the owner(s) or licensees of the adverse event and/or commercial information database(s) 12.

Practical, but non-limiting, examples of possible users of systems 10, 110 or 210 and the method depicted in FIG. 5, include manufacturers and/or distributors of medical products, holding companies, venture capital companies or other companies or individuals seeking to capitalize on ownership of a portfolio of new medical product information that may be of commercial value. The users may use the information to seek patent, or other intellectual property protection for the information. The systems 10, 110 and 210 and the methods depicted in FIGS. 5 and 6 are especially useful for creating proprietary information and products.

The systems and devices of the present invention can assist in preparing information for a patent application and can assist in documentation of the invention, including inventors, date of invention, progress of the development of invention. As used herein, proprietary information shall be construed to mean information that is used or intended to be used for establishing or claiming specific intellectual property rights. For example, the proprietary information can be used in the creation and protection of intellectual property, sale or licensing documents; that is, the proprietary information may comprise textual or graphical content that may be incorporated into patent applications. A 'proprietary new use' means a new use, in which one has or is seeking intellectual property rights, i.e., a patent.

It is not the intended purpose of this invention to encompass the simple copyrighting of package inserts that may contain adverse event information. A manufacturer and/or distributor is entitled to the copyright associated with any creative work that it produces, including package inserts. Of course, package inserts may contain adverse event information or product uses that are not proprietary and are in the public domain. The present invention is, therefore, not intended to encompass this practice. It is also not the intended purpose of the present invention to encompass proprietary kits (i.e., patented), wherein the kit is proprietary solely because of preexisting intellectual property rights. Rather, it is the intent of the invention to claim proprietary kits containing new proprietary adverse event information and/or instructions to use the product according to a proprietary new use based on new adverse event information, wherein that new adverse event information is the product of a system, device or method of the present invention.

Users might seek patent protection for new therapeutic uses for existing products based on newly discovered adverse event information. For any new use discovered by the systems according to the present invention, the instructions accompanying the product or device for which the new use is identified should desirably warn newly-identified high risk users of the product or device to avoid using it. Likewise, the instructions should also inform users who were previously, but wrongly, identified as high risk users that the product or device may be safely used by them. Preferably, systems 10, 110 and 210 are capable of formatting the proprietary information data, such that it is suitable for incorporation into the aforementioned intellectual property documents.

In FIG. 6, method steps 26', 28' and 30' are identical to their counterparts in FIG. 5. However, as indicated at step 32" of FIG. 6, the owner or user of the proprietary information commercializes the proprietary information by manufacturing and/or distributing (or causing to be manufactured and/or distributed) products or devices incorporating the proprietary information, and then selling the products or devices.

In addition to the functions represented by method steps 26', 28', 30', 32' and 32", additional tasks are preferably performed to more completely fulfil the purposes of the present invention, as reflected in FIGS. 5 and 6. For example, as indicated by step 29' in FIG. 5, server 14, 114 or 214 may be programmed to generate proprietary information, typically in textual and/or graphic form, that can be incorporated into intellectual property, sale and/or licensing documents. The documents then can be used in negotiations with product or device manufacturers and/or distributors or other interested third parties.

Additionally, FIG. 5 reveals in step 31' that server 14, 114 or 214 may optionally generate printed product warning information derived from the information database(s). The printed warning information or documentation may be used in connection with product packaging, such as, for example, product labeling or product packaging inserts to advise the consumer or user or responsible individual in the case of use by a child or animal (or doctor or prescriber in the case of medical products or devices requiring a prescription) of contraindications or other adverse events associated with use of the product or device. Alternatively, as shown in step 33' of FIG. 5, the owner of the proprietary information or its licensee may generate the aforesaid printed warning information.

Similarly, in FIG. 6, the server 14, 114 or 214 may generate proprietary information that may be incorporated into intellectual property and/or sale documents (step 31"). Printed product notices, product safety or warning information or documentation may also be generated by the servers 14, 114 or 214. Alternatively, as shown at step 33", this step may be performed by the owner or licensee of the proprietary information (who also manufactures and/or distributes the product or causes it to be manufactured or distributed).

Equipped with the new adverse event information generated by systems 10, 110 and 210, a user or competitors might also urge the FDA to compel existing manufacturers and/or distributors of a product or device to remove it from the market if the product or device does not have adequate safety warnings, or to prevent those contemplating marketing or distributing the product from entering the market without providing adequate safety labeling or documentation.

By "product warning information" or "product safety information" is meant any documentation, notice or warning, preferably in the form of a label or printed instruction, although verbal warnings, such as over the radio or television, or even doctor warnings. It is intended to, without limitation, include such warning information with regard to product or devices. It may be referred to as a 'product warning label,' 'labeling,' 'package insert,' 'material safety data sheet,' or 'product safety data sheet,' or any of a variety of recognized terms for documentation of information provided to the consumer, patient, subject or the like to inform them of safety concerns regarding the use of either a product or a device, particularly based upon the identification of new adverse event data. It is also intended to refer to such material provided for the parent of a child or owner of an animal, when the child or animal is the subject user of the product or device.

Nevertheless, the present invention is not intended to encompass pharmacogenomic techniques for detecting gene sequences associated with known adverse events. As referred to herein, genetic characteristics may include, e.g., skin color, height, hair color, blood type, and the like.

In a preferred application, the systems described herein may be used to develop new proprietary safer uses for drugs that are already generic or soon to become generic. A 'generic drug' means one in which the active compound either is not protected by a composition of matter patent, or the patent will very soon expire. Therefore the active compound is commercially available and adverse event data may be available from one or more sources. In some instances there are drugs that are on the market but protected by orphan drug status, such as thalidomide, or by a use patent, such as for AZT. In these instances the composition of matter patent had expired, but competitors have not entered the market because there are only a few known existing uses for the product, and these are covered by use patents or orphan drug provisions.

Nevertheless, such drugs may have been on the market for ten or more years and little research may have been conducted before or during that time to identify and optimize the fullest extent of their potential ranges of safe use. Moreover, they have probably been tested for other indications, and adverse event information exists on them.

In varying degrees, generics of a proprietary drug may differ from the proprietary drug itself, and from one another. More particularly, although their active ingredients may be the same, generic drugs may include impurities, inert substances, carriers and other agents that may not be present in their corresponding proprietary drugs or other generic alternatives thereof. When considering generics and their proprietary counterparts based solely on their active ingredients, the generics would be expected to exhibit similar adverse events. However, through implementation of the present invention, generic drugs can be precisely compared against their proprietary drug counterparts, and alternative generics, to determine the impact of their inactive ingredients on adverse events, despite the variability of such inactive ingredients. For instance, drugs with agents which delay the release of an active agent, prodrugs which are then converted into the active drug, or enantiomers of a chiral mixed drug, can be expected to exhibit many of the same side effects as drugs with the same active ingredient. In this context, therefore, a generic and a proprietary drug may be considered to be the same product if the adverse event(s) and/or new use(s) for the drugs would be expected to be consistent for both.

The "new use" derived from the new adverse event may involve restricting the use of the product or device in ways that are now discovered to be dangerous. For example, if a product is determined to be flammable or explosive, the "new proprietary use" would restrict its use in conditions that could lead to combustion or explosion, which may occur when used in the presence of an open flame or near a fire. Substances discovered to emit toxic fumes would, as a new use, only be utilized in well-ventilated areas, or under safety hoods. The new use may include providing a kit which contains warnings about a new adverse event relating to use of the product or device.

The term "commercially available" pertains to products or devices that are available to more than one group or company. The product can be a substance, such as a drug, which is known by more than one company or research group. With such a product or device, adverse event data may have been generated by more than one group, and adverse event data although generated by one group, may not be new. This is because another earlier group may have discovered the adverse event first. This is especially true when the product or device has been sold commercially, and is known to have been used by a number of different groups over time.

Studies may be performed with non-commercially available products, wherein a non-limiting example would be drugs. In this example, the non-commercially available drug may also be tested in patients receiving commercially available drugs. Drug interactions may be detected between the commercially available drug and the non-commercially available drug. In this situation the purpose of the study is to screen a database for adverse events of the non-commercially available product, not the commercially available product. A manufacturer and/or distributor of a commercially available product or device is not required to warn potential users about an interaction that may occur with their product or device and a product or device that is not yet available, or that the manufacturer or distributor does not even know exists. Unless specifically identified, this situation does not pertain to the present invention, which is intended for the screening of commercially available products or devices for adverse events.

Many entities, large and small, may beneficially utilize the systems described herein. A representative, although non-limiting, example would be an independent non-manufacturing company that procures access to one or more adverse event databases to analyze the data contained therein and identify new uses for existing drugs. The independent company could then license the "new use" technology it discovers to pharmaceutical manufacturers. The content of the licensing agreements may be agreed upon before or after the data has been analyzed. The independent company may opt to file appropriate intellectual property documents, such as patent applications covering the newly-discovered uses for the product and/or their attendant product warning information and receive monies derived from the sale of the drug in the form of royalties or a lump sum fee.

Alternatively, the independent company may utilize the services of a contract manufacturer that will make the drug for the independent company, which will reserve the right to sell the product on its own behalf. The independent company may also be a large medical insurer or pharmaceutical company that has access to its own extensive adverse event information database(s) from which may identify and commercially exploit new uses for existing medical products.

As mentioned above, the present systems and methods can also be utilized to develop proprietary safety information on products unrelated to the medical fields since manufacturers in other fields of endeavor generally are required to provide consumers with safety information regarding their products or devices.

Methods of Screening Adverse Events For Commercial Value

All adverse event information is not of equal value. "Commercial value" depends on the potential value of making a generic product or device into a proprietary product or device, or preventing a proprietary product or device from becoming a generic product or device. 'Potential commercial value' or 'commercial value,' as used herein, means whether it is in the financial interest of an individual or company to seek intellectual property rights on new adverse event information. It can also mean the quantifying of value or projected value based upon obtaining intellectual property rights to the adverse event information. Determining potential commercial value is not intended to encompass the practice of determining product liability based on discovering a new adverse event; nor is it intended to encompass the estimation of loss of sales due to the identification of a new adverse event; nor is it intended to encompass the potential competitive advantage of a competing product based on the discovery of a new adverse event. Instead, estimation or determination of commercial value in this invention is intended to encompass the practice of determining the increased profitability from extending or developing new intellectual property rights based on the development of a new use or a proprietary kit containing the new adverse event information.

If a proprietary product or device is loosing money or marginally profitable, then extending its proprietary status by discovering new adverse events will add little value. For example, discovering an adverse event in a generic aluminum-containing antacid may not bring much added profit, even if the product were to become proprietary, if consumers were more interested in switching to other antacids lacking aluminum, such as calcium-based antacids or magnesium-based antacids. Alternatively, a consumer with gastritis who is faced with the proposition of buying expensive antacids, may prefer to use alternative newer, more expensive, and more effective products, such as histamine blockers or hydrogen pump inhibitors. Alternatively, large profits can be made on a highly profitable patented product or device by extending its proprietary status by obtaining one or more new patents based upon the discovery of adverse events associated with use of the product or device.

A manufacture and/or distributor may be planning to sell a new improved product having a different physical property ("characteristic") from that of the previously existing product. In this instance, the manufacture or distributor may not want to compete with the pre-existing product after the patent expires (the product may be owned by the same or a different owner). In this situation the manufacturer or distributor may find it advantageous and in its best financial interest to develop a "new" use for the pre-existing product based on the discovery of a new adverse event relating to use of the product.

In a preferred embodiment of the invention, a product or device for which an adverse event is discovered, is also one that is highly profitable, but would face a marked decrease in profitability if the product or device were to lose its proprietary status. One skilled in the art can screen products or devices by recognized methods to determine the potential value of discovering proprietary adverse events. Those skilled in, e.g., sales, marketing, licensing, statistics or business practices, will know how to use recognized methods to calculate or estimate such parameters as, in the non-limiting examples of, current market share, potential market share, total market share in unit volume or sales, marketing costs, elasticity of demand, cost of production, cost of marketing, number of competitors, market potential, cost of discovering a new adverse event, product liability costs, growth of market and the like. Mathematical modeling, with or without the use of computers, can be performed to evaluate whether it would be profitable to develop a proprietary new use based on a new adverse event. In addition to profitability, an entity may desire to determine cost of capital and opportunity costs before deciding to move forward with the project.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art. Reference to known method steps, conventional method steps, known methods or conventional methods is not in any way an admission that any aspect, description or embodiment of the present invention is disclosed, taught or suggested in the relevant art.

Any description of a class or range as being useful or preferred in the practice of the invention shall be deemed a description of any subclass or subrange contained therein, as well as a separate description of each individual member or value in said class or range.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A system for creating and using data associated with a commercially available product, comprising:

at least one database, comprising together or separately, adverse event data associated with exposure to or use of the product and commercial data regarding marketing, sales, profitability or related information pertaining to the product;

a processor for accessing and analyzing data regarding a plurality of different adverse events from the at least one adverse event databases to assist in identifying (i) at least one new adverse event associated with exposure to or use of the product, (ii) at least one new use for the product responsive to identification of the at least one new adverse event; and (iii) the potential commercial value of the at least one new use for the product;

an adverse event information storage device for storing the new adverse event data of potential commercial value identified with the assistance of the processor;

a user node for making requests for adverse event information to, and for receiving adverse event information from the processor; and a user interface for interfacing the processor and the user node.

2. The system of claim 1, wherein the processor, and the adverse event information storage device reside on a server, and wherein at least one adverse event database also resides on the server.

3. The system of claim 1, wherein the processor, and the adverse event information storage device reside on a server, but wherein at least one adverse event database does not reside on the server.

4. The system of claim 1, wherein at least one adverse event database comprises raw data from a plurality of different adverse events.

5. The system of claim 1, wherein data from at least one database comprises previously known or reported adverse event information regarding exposure to or use of the product.

6. The system of claim 5, wherein at least one source of adverse event data further comprises information regarding adverse events selected from the group consisting of death, illness, hospitalization, missed work, medical costs, abnormal laboratory results and surgeries.

7. The system of claim 5, wherein at least one database comprises raw adverse event data linked with exposure to or use of the product.

8. The system of claim 7, wherein at least one database comprises information relating to patents and patent applications.

9. The system of claim 7, wherein at least one database further comprises raw data regarding at least one beneficial attribute of the product.

10. The system of claim 1, wherein at least one adverse event database further comprises comparative adverse event data for (i) target groups exposed to or using the product, and (ii) control groups not exposed to or using the product.

11. The system of claim 1, wherein at least one adverse event database comprises adverse event data gathered from at least about 5000 subjects.

12. The system of claim 11, wherein the at least one adverse event database further comprises information regarding amount of use of the product or duration of exposure to the product by each subject.

13. The system of claim 11, wherein the at least one adverse event database further comprises information regarding product post-exposure adverse event data, which is recorded in selected time increments, ranging from less than one hour to more than ten years.

14. The system of claim 1, wherein the processor further comprises a means for commercializing at least one new use for the product after determining at least one new adverse event associated with exposure to or use of the product in consideration of potential commercial value of the new use.

15. The system of claim 14, wherein commercialization comprises facilitating selling, leasing or licensing the newly identified product information.

16. The system of claim 14, wherein commercialization comprises facilitating protecting intellectual property interests in the newly identified product information.

17. The system of claim 14, wherein commercialization comprises formatting the data relating to at least one new adverse event associated with exposure to or use of the product, or documenting same, such that a manufacturer or distributor of the product must inform consumers, users or individuals responsible for the user, physicians or prescribers about at least one new adverse event associated with exposure to or use of the product.

18. The system of claim 1, wherein the new use comprises restricting exposure of the product to one of the high risk associated groups consisting of high or low temperatures, chemicals, surfaces, pressures, electricity and sparks; or contact of the product with one of the group consisting of skin, eyes, ears, respiratory surfaces, gastrointestinal surfaces and mucous membranes of the consumer, or to a subpopulation group selected from the group consisting of children, pregnant women, consumers with specific allergies or medical conditions and animals; or to a subpopulation defined by at least one consumer-identifying characteristic selected from the group consisting of sex, weight, age, race, genetic characteristics, medical condition, pregnancy status, presence of allergies, and use of medicines or medical devices.

19. The system of claim 1, wherein the product is a medical product.

20. The system of claim 19, wherein the medical product is a drug.

21. The system of claim 20, wherein the drug is a generic drug.

22. The system of claim 1, wherein the product is a non-medical product.

23. A proprietary new use for a commercially available product, wherein the new use is determined from the data provided by the system of claim 1.

24. A proprietary new use for a commercially available product according to claim 23, without a need for an experimental or clinical study to verify the at least one new adverse event or to test the new use.

25. A proprietary new use for a commercially available product according to claim 23, wherein an experimental or clinical study to verify the at least one new adverse event or to test the new use is required.

26. The proprietary new use for a commercially available product according to claim 23, wherein the new use is protected as an intellectual property.

27. A proprietary new use for a commercially available product according to claim 23, wherein the use is restricted to one or more subgroups of consumers, wherein the use is based on demographic data, and for which use additional testing of the consumers is not needed.

28. The proprietary new use of the product according to claim 23, wherein at least one new adverse event comprises a drug interaction.

29. The proprietary new use of the product according to claim 23, wherein the at least one new adverse event is based upon neither a drug interaction, nor a chronic immune mediated disorder.

30. A proprietary kit comprising (i) product and (ii) documentation notifying a user of the product of at least one new adverse event relating to the product, wherein determination of the new adverse event is based upon the data provided by the system of claim 1.

31. A proprietary kit comprising (i) product and (ii) documentation notifying a user of the product of at least one new adverse event relating to the proprietary new use of a product, wherein the proprietary new use is in accordance with claim 27.

32. A proprietary kit comprising (i) product and (ii) documentation notifying a user of the product of at least one new adverse event relating to the proprietary new use of a product, wherein the proprietary new use is in accordance with claim 29.

33. A method for creating and using data associated with a commercially available product, wherein the method comprises the steps of:
   accessing at least one data source, comprising together or separately, adverse event data associated with exposure to or use of the product and commercial data regarding marketing, sales, profitability or related information pertaining to the product;
   analyzing the accessed data to identify (i) at least one new adverse event associated with exposure to or use of the product, (ii) at least one new use for the product responsive to identification of the at least one new adverse event, and (iii) the potential commercial value of the at least one new use for the product; and
   commercializing the newly identified product information based upon the analyzed data.

34. The method of claim 33, wherein the commercializing step comprises selling, leasing or licensing the newly identified product information.

35. The method of claim 33, wherein the commercializing step comprises protecting the intellectual property interest in the newly identified product information.

36. The method of claim 33, wherein the commercializing step comprises formatting the data relating to at least one new adverse event associated with exposure to, or use of the product, or documenting same, such that a manufacturer or distributor of the product must inform consumers, users or individuals responsible for the user, physicians or prescribers about at least one new adverse event associated with exposure to or use of the product.

37. The method of claim 33, wherein at least one adverse event information data source further comprises comparative adverse event data for (i) target groups exposed to or using the product, and (ii) control groups not exposed to or using the product.

38. The method of claim 33, wherein at least one adverse event data source comprises adverse event data gathered from at least about 5000 subjects.

39. The method of claim 38, wherein the at least one adverse event source further comprises information regarding amount of use of the product or duration of exposure to the product by each subject.

40. The method of claim 38, wherein the at least one adverse event source further comprises information regarding product post-exposure adverse event data, which is recorded in selected time increments, ranging from less than one hour to more than ten years.

41. The method of claim 38, wherein at least one adverse event data source further comprises information regarding adverse events selected from at least two categories selected from the group consisting of death, illness, hospitalization, missed work, medical costs, abnormal laboratory results and surgeries.

42. The method of claim 33, wherein at least one new use of the product is a restricted use in at least one population subgroup, wherein there is observed to be a high risk of at least one adverse event associated with exposure to or use of the product.

43. The method of claim 33, wherein the new use comprises restricting exposure of the product to one of the high risk associated groups consisting of high or low temperatures, chemicals, surfaces, pressures, electricity and sparks; or contact of the product with one of the group consisting of skin, eyes, ears, respiratory surfaces, gastrointestinal surfaces and mucous membranes of the consumer, or to a subpopulation group selected from the group consisting of children, pregnant women, consumers with specific allergies or medical conditions and animals; or to a subpopulation defined by at least one consumer-identifying characteristic selected from the group consisting of sex, weight, age, race, genetic characteristics, medical condition, pregnancy status, presence of allergies, and use of medicines or medical devices.

44. The method of claim 33, wherein at least one adverse event data source comprises raw data from a plurality of different adverse events.

45. The method of claim 44, wherein data from at least one data source comprises adverse event information regarding exposure to or use of the product.

46. The method of claim 44, wherein at least one data source comprises information relating to patents and patent applications.

47. The method of claim 44, wherein at least one data source further comprises raw data regarding at least one beneficial attribute of the product.

48. The method of claim 33, wherein the product is a medical product.

49. The method of claim 48, wherein the medical product is a drug.

50. The method of claim 49, wherein the drug is a generic drug.

51. The method of claim 33, wherein the product is a non-medical product.

52. A proprietary new use for a commercially available product, wherein the new use is determined from the data provided by the method of claim 33.

53. A proprietary new use for a commercially available product according to claim 52, without a need for an experimental or clinical study to verify the at least one new adverse event or to test the new use.

54. A proprietary new use for a commercially available product according to claim 52, wherein an experimental or clinical study to verify the at least one new adverse event or to test the new use is required.

55. The proprietary new use for a commercially available product according to claim 52, wherein the new use is protected as an intellectual property.

56. A proprietary new use for a commercially available product according to claim 52, wherein the use is in one or more subgroups of consumers, wherein the use is based on demographic data, and for which use additional testing of the consumers is not needed.

57. The proprietary new use of the product according to claim 56, wherein at least one new adverse event comprises a drug interaction.

58. The proprietary new use of the product according to claim 56, wherein at least one new adverse event is based upon neither a drug interaction, nor a chronic immune mediated disorder.

59. A proprietary kit comprising (i) product and (ii) documentation notifying a user of the product of at least one new adverse event relating to the product, wherein determination of the new adverse event is based upon the data provided by the method of claim 33.

60. A proprietary kit comprising (i) product and (ii) documentation notifying a user of the product of at least one new adverse event relating to the proprietary new use of a product, wherein the proprietary new use is determined from the data provided in accordance with claim 53.

61. A proprietary kit comprising (i) product and (ii) documentation notifying a user of the product of at least one new adverse event relating to the proprietary new use of a product, wherein the proprietary new use is determined from the data provided in accordance with claim 54.

62. A method of establishing at least one commercial new use for a commercially available product, wherein the method comprises the steps of:

identifying at least one adverse event associated with exposure to or use of the product;

comparing the at least one adverse event with reported or previously known adverse event data associated with exposure to or use of the product;

determining that the identified at least one adverse event is a new adverse event associated with exposure to or use of the product;

analyzing the new adverse event to identify at least one new use for the product responsive to identification of the at least one new adverse event;

accessing at least one data source comprising commercial data regarding marketing, sales, profitability or related information pertaining to the product; and determining potential commercial value of the at least one new use for the product based upon the accessed commercial data.

63. The method of claim 62, wherein the at least one new use of the product is a restricted use in at least one population subgroup, wherein there is observed to be a high risk of at least one adverse event associated with exposure to or use of the product.

64. The method of claim 62, wherein the new use comprises restricting exposure of the product to one of the high risk associated group consisting of high or low temperatures, chemicals, surfaces, pressures, electricity and sparks; or contact of the product with one of the group consisting of skin, eyes, ears, respiratory surfaces, gastrointestinal surfaces and mucous membranes of the consumer, or to a subpopulation group selected from the group consisting of children, pregnant women, consumers with specific allergies or medical conditions and animals; or to a subpopulation defined by at least one consumer-identifying characteristic selected from the group consisting of sex, weight, age, race, genetic characteristics, medical condition, pregnancy status, presence of allergies, and use of medicines or medical devices.

65. The method of claim 62, wherein the known adverse event data comprises raw data from a plurality of different adverse events sources.

66. The method of claim 65, wherein data from at least one data source comprises adverse event information regarding exposure to or use of the product.

67. The method of claim 65, wherein at least one source of known adverse event data comprises information relating to patents and patent applications.

68. The method of claim 65, further comprising at least one source of raw data regarding at least one beneficial attribute of the product.

69. The method of claim 65, wherein at least one source of the known adverse event data, further comprises information regarding adverse events selected from the group consisting of death, illness, hospitalization, missed work, medical costs, abnormal laboratory results and surgeries.

70. The method of claim 62, further comprising commercializing the at least one new use for the product after determining at least one new adverse event associated with exposure to or use of the product in consideration of potential commercial value of the new use.

71. The method of claim 70, wherein the commercializing step comprises selling, leasing or licensing the newly identified product information.

72. The method of claim 70, wherein commercializing step comprises protecting the intellectual property interest in the newly identified product information.

73. The method of claim 70, wherein the commercializing step comprises formatting the data relating to at least one new adverse event associated with exposure to or use of the product, or documenting same, such that a manufacturer or distributor of the product must inform consumers, users or individuals responsible for the user, physicians or prescribers about the at least one new adverse event associated with exposure to or use of the product.

74. The method of claim 62, wherein the product is a medical product.

75. The method of claim 74, wherein the medical product is a drug.

76. The method of claim 75, wherein the drug is a generic drug.

77. The method of claim 62, wherein the product is a non-medical product.

78. A proprietary new use for a commercially available product, wherein the new use is determined from the data provided by the method of claim 62.

79. A proprietary new use for a commercially available product according to claim 78, without a need for an experimental or clinical study to verify the at least one new adverse event or to test the new use.

80. A proprietary new use for a commercially available product according to claim 78, wherein an experimental or clinical study to verify the at least one new adverse event or to test the new use is required.

81. A proprietary new use for a commercially available product according to claim 78, wherein the use is in one or more subgroups of consumers, wherein the use is based on demographic data, and for which use additional testing of the consumers is not needed.

82. The proprietary new use of the product according to claim 78, wherein at least one new adverse event comprises a drug interaction.

83. The proprietary new use of the product according to claim 78, wherein at least one new adverse event is based upon neither a drug interaction, nor a chronic immune mediated disorder.

84. A proprietary kit comprising (i) product and (ii) documentation notifying a user of the product of at least one new adverse event relating to the product, wherein determination of the new adverse event is based upon the data provided by the method of claim 62.

85. A proprietary kit comprising (i) product and (ii) documentation notifying a user of the product of at least one new adverse event relating to the product, wherein determination of the new adverse event is in accordance with claim 68.

86. A proprietary kit comprising (i) product and (ii) documentation notifying a user of the product of at least one new adverse event relating to the product, wherein determination of the new adverse event is in accordance with claim 72.

87. A device for processing and managing product-related data, comprising:
    a computer-readable signal-bearing medium;
    means in the medium for accessing data regarding a plurality of adverse events from at least one database, comprising together or separately, adverse event data associated with exposure to or use of a commercially available product, and wherein at least one database comprises commercial data regarding marketing, sales, profitability or related information pertaining to the product
    means in the medium for processing data regarding a plurality of adverse events from the at least one database to assist in identifying (i) at least one new adverse event associated with exposure to or use of the product, (ii) at least one new use for the product responsive to identification of the at least one new adverse event; and (iii) the potential commercial value of the at least one new use for the product;
    means in the medium for storing new adverse event data of potential commercial value; and
    means in the medium for requesting and for receiving new adverse event data.

88. The device of claim 87, further comprising means in the medium for interfacing the processor means with a user node, wherein at least one adverse event database resides on the computer.

89. The device of claim 87, further comprising means in the medium for interfacing the processor means with a user node, wherein at least one adverse event database does not reside on the computer.

90. The device of claim 87, wherein the at least one database contains previously known or reported adverse event data associated with exposure to or use of the product.

91. The device of claim 87, wherein the at least one database contains raw adverse event data associated with exposure to or use of the product.

92. The device of claim 91, wherein the at least one database contains information relating to patents and patent applications.

93. The device of claim 91, wherein the at least one database contains data regarding at least one beneficial attribute of the product.

94. The device of claim 92, wherein the at least one database contains information regarding adverse events selected from the group consisting of death, illness, hospitalization, missed work, medical costs, abnormal laboratory results and surgeries.

95. The device of claim 87, further comprising means for commercializing at least one new use for the product after determining at least one new adverse event associated with exposure to or use of the product in consideration of the potential commercial value of the new use.

96. The device of claim 95, wherein commercializing means comprises means for selling, leasing or licensing the newly identified product information.

97. The device of claim 95, wherein commercializing means comprises means for protecting the intellectual property interest in the newly identified product information.

98. The device of claim 95, wherein commercializing means comprises means for formatting the data relating to at least one new adverse event associated with exposure to or use of the product, or means for documenting same, such that a manufacturer or distributor of the product must inform consumers, users or individuals responsible for the user, physicians or prescribers about at least one new adverse event associated with exposure to or use of the product.

99. The device of claim 87, wherein the data accessed by the means in the medium, further comprises means for comparing adverse event data between (i) target groups exposed to or using the product, and (ii) control groups not exposed to or using the product.

100. The device of claim 87, wherein the data accessed by the means in the medium comprises adverse event data gathered from at least about 5,000 subjects.

101. The device of claim 100, wherein adverse event data accessed by the means in the medium, further comprises information regarding amount of use of the product or duration of exposure to the product by each subject.

102. The device of claim 101, wherein adverse event data accessed by the means in the medium, further comprises information regarding product post-exposure adverse event data, which is recorded in selected time increments, ranging from less than one hour to more than ten years.

103. The device of claim 87, wherein the product is a medical product.

104. The device of claim 103, wherein the medical product is a drug.

105. The device of claim 104, wherein the drug is a generic drug.

106. The system of claim 87, wherein the product is a non-medical product.

107. A proprietary new use for a commercially available product, wherein the new use is determined from the data provided by use of the device of claim 87.

108. A proprietary new use for a commercially available product according to claim 107, without a need for an experimental or clinical study to verify the at least one new adverse event or to test the new use.

109. A proprietary new use for a commercially available product according to claim 108, wherein an experimental or clinical study to verify the at least one new adverse event or to test the new use is required.

110. A proprietary new use for a commercially available product according to claim 108, wherein the use is in one or more subgroups of consumers, wherein the use is based on demographic data, and for which use additional testing of the consumers is not needed.

111. The proprietary new use of a product according to claim 107, wherein the new adverse event comprises a drug interaction.

112. The proprietary new use of a product according to claim 107, wherein the new adverse event is based upon neither a drug interaction, nor a chronic immune mediated disorder.

113. A proprietary kit comprising (i) product and (ii) documentation notifying a user of the product of the at least one new adverse event relating to the product, wherein determination of the new adverse event is based upon the data provided by use of the device of claim 87.

114. A proprietary kit comprising (i) product and (ii) documentation notifying a user of the product of the at least one new adverse event relating to the new use of a product, wherein the new use is in accordance with claim 95.

115. The proprietary new use for a commercially available product according to claim 107, wherein the new use is protected as an intellectual property.

116. The proprietary new use for a commercially available product according to claim 78, wherein the new use is protected as an intellectual property.

117. A proprietary new use of claim 23, wherein the new use is one other than other than a new dosing regimen.

118. A proprietary new use of claims 52, wherein the new use is one other than other than a new dosing regimen.

119. A proprietary kit comprising (i) product and (ii) documentation notifying a user of the product of the at least one new adverse event relating to the proprietary new use of a product, wherein the proprietary new use is in accordance with claim 118.

120. A proprietary new use of claims 78, wherein the new use is one other than a other than a new dosing regimen.

121. A proprietary new use of claims 107, wherein the new use is one other than a new dosing regimen.

122. The system of claim 6, wherein at least one database comprises raw data on a plurality of different adverse events linked with exposure to or use of the product.

123. The method of claim 41, wherein at least one data source comprises raw data on a plurality of different adverse events linked with exposure to or use of the product.

124. The method of claim 65, wherein at least one database comprises raw data on a plurality of different adverse events linked with exposure to or use of the product.

125. The device of claim 95, wherein at least one database comprises raw data on a plurality of different adverse events linked with exposure to or use of the product.

126. The system of claim 1, wherein at least one database comprises raw commercial data.

127. The method of claim 35, wherein at least one database comprises raw commercial data.

128. The method of claim 62, wherein at least one database comprises raw commercial data.

129. The device of claim 87, wherein at least one database comprises raw commercial data.

130. The system of claim 16, wherein commercialization comprises facilitating documentation of inventorship.

131. The method of claim 33, wherein commercializing further comprises documenting inventorship.

132. The method of claim 70, wherein commercializing further comprises documenting inventorship.

133. The device of claim 95, wherein means for commercializing further comprises means for facilitating documentation of inventorship.

134. The system of claim 130, further comprising facilitating documentation of date of inventorship.

135. The method of claim 131, further comprising documenting date of inventorship.

136. The method of claim 132, further comprising documenting date of inventorship.

137. The device of claim 133, further comprising a means for facilitating documentation of date of inventorship.

* * * * *

US006584472C1

(12) EX PARTE REEXAMINATION CERTIFICATE (7900th)
United States Patent
Classen

(10) Number: US 6,584,472 C1
(45) Certificate Issued: *Nov. 30, 2010

(54) METHOD, SYSTEM AND ARTICLE FOR CREATING AND MANAGING PROPRIETARY PRODUCT DATA

(75) Inventor: John Barthelow Classen, Baltimore, MD (US)

(73) Assignee: Classen Immunotherapies, Inc., Baltimore, MD (US)

Reexamination Request:
No. 90/007,639, Jul. 22, 2005

Reexamination Certificate for:
Patent No.: 6,584,472
Issued: Jun. 24, 2003
Appl. No.: 09/804,289
Filed: Mar. 12, 2001

(*) Notice: This patent is subject to a terminal disclaimer.

Related U.S. Application Data

(63) Continuation-in-part of application No. 09/449,178, filed on Nov. 24, 1999, now Pat. No. 6,219,674.

(51) Int. Cl.
*G06F 19/00* (2006.01)

(52) U.S. Cl. .......................... 707/770; 600/300; 705/3; 707/923; 707/941; 707/944; 707/999.104

(58) Field of Classification Search .................. 705/2, 705/3; 707/104.1, 300, 100
See application file for complete search history.

(56) References Cited

U.S. PATENT DOCUMENTS

| | | | |
|---|---|---|---|
| 3,993,767 A | 11/1976 | Alphin et al. | |
| 4,034,083 A | 7/1977 | Mattson | |
| 4,596,812 A | 6/1986 | Chidsey, III et al. | |
| 5,536,506 A | 7/1996 | Majeed et al. | |
| 5,737,539 A | 4/1998 | Edelson | |
| 5,744,161 A | 4/1998 | Majeed et al. | |
| 5,845,255 A | 12/1998 | Mayaud | |
| 6,465,463 B1 | 10/2002 | Cohn et al. | |
| 6,469,012 B1 | 10/2002 | Ellis et al. | |
| 6,784,177 B2 | 8/2004 | Cohn et al. | |
| 7,069,226 B1 * | 6/2006 | Kleinfelter ...................... 705/2 |

OTHER PUBLICATIONS

"Computerized surveillance of advance drug events in hospital patients", JAMA, 1991 266–2847–2851I, David Classen et al. (Classen '91–1).*

"Surveillance for Quality Assessment: IV: Surveillance Using a Hospital Information System", Source: Infection Control and Hospital Epidemiology, vol. 12, No. 4 (Apr. 1991), pp. 239–244, Published by: The University of Chicago Press (Stable URL: http://www.jostor.org/stable/301466998), David Classen et al. (Classen'91–2).*

(Continued)

*Primary Examiner*—Majid A. Banankhah

(57) ABSTRACT

The mechanism comprises systems, methods and computerized data management device for creating and using data relating to a medical or non-medical product or device to enhance the safety of the product or device. Vast amounts of data is received regarding adverse events associated with a particular product or device, which data is analyzed in light of known adverse events associated with the product or device. At least one proprietary database of newly discovered adverse event information is created and utilized, and new characteristics of or uses for the product or device are determined. Adverse event information is gathered for a large number of population sub-groups. The system may also be programmed to incorporate the information into intellectual property and contract documents. Manufacturers and/or distributors can include the proprietary information in consumer safety information, which accompanies the product or device, or which is provided to patients, users, consumers and the like, or in the case of certain medical products or devices, to prescribers of those products or devices.

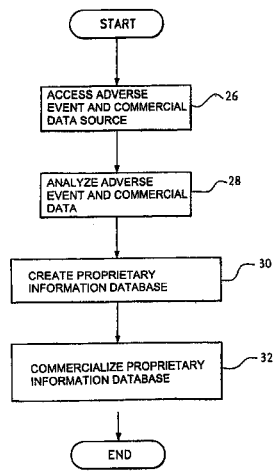

OTHER PUBLICATIONS

"Using A Hospital Information System To Access The Effect Of Adverse Drug Events", Clinical Epidemiology, Medical Informatics, and Pharmacy LDS Hospital and University of Utah School of Medicine Salt Lake City, Utah, JAMIA 1993, David Classen et al. (Classen '93).*

Federal Register, vol. 58, No. 105, (Jun. 3, 1993).

Baker v. Secretary of Department of Health and Human Services, 2003 WL 22416622, Sep. 26, 2003.

"Post–marketing surveillance for adverse events after vaccination: the national Vaccine Adverse Event Reporting System (VAERS)," Medwatch Continuing Education Article, Nov. 1998.

Vaccine Safety Forum, Summaries of Two Workshops, National Academy Press, Washington, D.C., 1997.

"What Is A Serious Adverse Event?," http://www.fda.gov/medwatch/report/DESK/adevnt.htm.

Chen, R. et al., "Vaccine Safety Datalink Project: A New Tool for Improving Vaccine Safety Monitoring in the United States," Pediatrics, vol. 99, No. (?), pp. 765–773, Jun. 1997.

Classen, D. et al., "Description of a Computerized Adverse Drug Event Monitor Using a Hospital Information System," Hosp Pharm, 1992, 27:774–779, 783.

Classen, D. et al., "Computerized Surveillance of Adverse Drug Events in Hospital Patients," JAMA, Nov. 1991, 266:20, pp. 2847–2851.

Classen, D. et al., "Adverse Drug Events in Hospitalized Patients," JAMA, Jan. 1997, 227:4, pp. 301–306.

Classen, D. et al., "The Computer–Based Patient Record," Hospital Epidemiology and Infection Control, $2^{nd}$ Ed., Lippincott Williams & Wilkins, Philadelphia, 1999, pp. 141–154.

Ellenberg, S., "Statement . . . Before the Subcommittee on National Security, Veterans Affairs, and International Relations Committee on Government Reform, U.S. House of Representatives, Jul. 21, 1999" (www.fda.gov/ola/1999/anthrax.html).

Evans, R. et al., Development of Computerized Adverse Drug Event Monitor, $15^{th}$ Annual Symposium of Computer Applications in Medical Care, Nov. 1991, AIMA, Inc., 1992, pp. 23–27.

Evans, R. et al., "Prevention of Adverse Drug Events through Computerized Surveillance," $16^{th}$ Annual Symposium of Computer Applications in Medical Care, Nov. 1992, AIMA, Inc., 1993, pp. 437–441.

Evans, R. et al., "Preventing Adverse Drug Events in Hospitalized Patients," Ann. Pharm., Apr. 1994, 28, pp. 523–527.

Evans, R. et al., "Evaluation of a Computer Assisted Antibiotic–Dose Monitor," Annals. Pharm., Oct. 1999, 33, pp. 1026–1031.

Evans, R., et al., "Using a Hospital Information System To Assess The Effects Of Adverse Drug Events," $17^{th}$ Annual Symposium on Computer Applications in Medical Care, Oct. 1993, pp. 161–165.

Evans, R. et al., "A Computer–Assisted Management program for Antibiotics and Other Antiinfective Agents," 338 The New England Journal of Medicine, 232–238 (1998).

Kling, J., "From hypertension to angina to Viagra," Modern Drug Discovery, Nov./Dec. 1998, 1(2), pp. 31, 33–34, 36, 38. The American Chemical Society (1998).

Lindquist, M. et al., "From Association to Alert—A Revised Approach to International Signal Analysis," Pharmacoepidemiolgy and Drug Safety, 8:S15–S25 (Apr. 1999).

Morrow, D., "New Profits in Old Bottles," The New York Times (3 pages), Friday, Mar. 19, 1999.

Naranjo, C. et al., "A method for estimating the probability of adverse drug reactions," Clin Pharmacol Ther., 30:2, Aug. 1981, pp. 239–245.

Pinkston, V. et al., "Management of Adverse Drug Reaction and Adverse Event Data through Collection, Storage and Retrieval," Detection of New Adverse Drug Reactions, $4^{th}$ Ed., pp. 218–296, London: Macmillan Reference Ltd., Apr. 1998.

Szarfman, A., "Proceedings of the Biopharmaceutical Section," Abstract, American Statistical Association, pp. 12–13, Alexandria, Virginia (1999).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 17, 36, 73 and 98 is confirmed.

Claims 1-16, 18-35, 37-41, 44-47, 52-58, 60-72, 78-83, 85-97, 99-102, 107-121, 128-129, 132-133 and 136-137 are cancelled.

Claims 42-43, 48-51, 59, 74-77, 84, 103-106, 122-127 and 130-131 are determined to be patentable as amended.

Claims 134 and 135, dependent on an amended claim, are determined to be patentable.

42. The method of claim [33] *36*, wherein at least one new use of the product is a restricted use in at least one population subgroup, wherein there is observed to be a high risk of at least one adverse event associated with exposure to or use of the product.

43. The method of claim [33] *36*, wherein the new use comprises restricting exposure of the product to one of the high risk associated groups consisting of high or low temperatures, chemicals, surfaces, pressures, electricity and sparks; or contact of the product with one of the group consisting of skin, eyes, ears, respiratory surfaces, gastrointestinal surfaces and mucous membranes of the consumer, or to a subpopulation group selected from the group consisting of children, pregnant women, consumers with specific allergies or medical conditions and animals; or to a subpopulation defined by at least one consumer-identifying characteristic selected from the group consisting of sex, weight, age, race, genetic characteristics, medical condition, pregnancy status, presence of allergies, and use of medicines or medical devices.

48. The method of claim [33] *36*, wherein the product is a medical product.

49. The method of claim [48] *36*, wherein the medical product is a drug.

50. The method of claim [49] *36*, wherein the drug is a generic drug.

51. The method of claim [33] *36*, wherein the product is a non-medical product.

59. A proprietary kit comprising (i) product and (ii) documentation notifying a user of the product of at least one new adverse event relating to the product, wherein determination of the new adverse event is based upon the data provided by the method of claim [33] *36*.

74. The method of claim [62] *73*, wherein the product is a medical product.

75. The method of claim [74] *73*, wherein the medical product is a drug.

76. The method of claim [75] *73*, wherein the drug is a generic drug.

77. The method of claim [62] *73*, wherein the product is a non-medical product.

84. A proprietary kit comprising (i) product and (ii) documentation notifying a user of the product of at least one new adverse event relating to the product, wherein determination of the new adverse event is based upon the data provided by the method of claim [62] *73*.

103. The device of claim [87] *98*, wherein the product is a medical product.

104. The device of claim [103] *98*, wherein the medical product is a drug.

105. The device of claim [104] *98*, wherein the drug is a generic drug.

106. The system of claim [87] *98*, wherein the product is a non-medical product.

122. The system of claim [6] *17*, wherein at least one database comprises raw data on a plurality of different adverse events linked with exposure to or use of the product.

123. The method of claim [41] *36*, wherein at least one data source comprises raw data on a plurality of different adverse events linked with exposure to or use of the product.

124. The method of claim [65] *74*, wherein at least one database comprises raw data on a plurality of different adverse events linked with exposure to or use of the product.

125. The device of claim [95] *98*, wherein at least one database comprises raw data on a plurality of differnet adverse events linked with exposure to or use of the product.

126. The system of claim [1] *17*, wherein at least one database comprises raw commercial data.

127. The method of claim [35] *36*, wherein at least one database comprises raw commercial data.

130. The system of claim [16] *17*, wherein commercialization comprises facilitating documentation of inventorship.

131. The method of claim [33] *36*, wherein commercializing further comprises documenting inventorship.

\* \* \* \* \*